United States Patent [19]

D'Ambra et al.

[11] Patent Number: 5,068,234

[45] Date of Patent: Nov. 26, 1991

[54] 3-ARYLCARBONYL-1-(C-ATTACHED-N-HETERYL)-1H-INDOLES

[75] Inventors: Thomas E. D'Ambra, North Greenbush; Edward R. Bacon; Malcolm R. Bell, both of East Greenbush; Philip M. Carabateas, Schodack; Michael A. Eissenstat, West Sand Lake; Virendra Kumar, Colonie; John P. Mallamo, Kinderhook Township, Columbia County; Susan J. Ward, East Greenbush, all of N.Y.

[73] Assignee: Sterling Drug Inc., New York, N.Y.

[21] Appl. No.: 484,759

[22] Filed: Feb. 26, 1990

[51] Int. Cl.$^5$ .................. C07D 417/06; C07D 413/06; A61K 31/54; A61K 31/535

[52] U.S. Cl. ................. 514/235.2; 514/228.2; 544/61; 544/143

[58] Field of Search ............... 548/491; 544/61, 143; 514/228.2, 235.2

[56] References Cited

U.S. PATENT DOCUMENTS

| Re. 32,761 | 10/1988 | Bell | 544/143 |
|---|---|---|---|
| 3,489,770 | 1/1970 | Herbst | 544/143 |
| 3,946,029 | 3/1976 | Deschamps et al. | 424/263 |
| 4,139,634 | 2/1979 | Pigevol | 544/143 |
| 4,581,354 | 4/1986 | Bell | 544/121 |
| 4,634,776 | 1/1987 | Bell | 548/193 |

OTHER PUBLICATIONS

Inion et al., Europ. J. of Med. Chem., 10(3), 276–285 (1975).
Tambute, Acad. Sci. Comp. Rend., Ser. C 278(20), 1239–1242 (1974).
Dalla Croce, Chem. Abst., 80, 95655f (1974).
Bosch et al., Tetrahedron, 40(8), 1419–24 (1984).
Bosch et al., J. Org. Chem., 48(25), 4836–41 (1983).
Bennasar et al., Tetrahedron, 42(2), 637–647 (1986).
Vartangan et al., Ann. Khim. Zh., 38(5), 308–313 (1985).
Chem. Abst. 105, 114874e (1985).
Nilsson et al., Acta. Chem. Scand., Ser. B, B39(7), 531–537 (1985).
Sasakura et al., Syn. Comm. 18(3), 265–273 (1988).

*Primary Examiner*—C. Warren Ivy
*Assistant Examiner*—Celia Chang
*Attorney, Agent, or Firm*—William G. Webb; Paul E. DuPont

[57] ABSTRACT

2-$R_2$-$R_4$-substituted-3-$R_3$-CO-1-[(C-attached-N-herteryl)-(Alk)$_n$]-1H-indoles useful as analgesic, anti-rheumatic, anti-inflammatory or anti-glaucoma agents.

18 Claims, No Drawings

3-ARYLCARBONYL-1-(C-ATTACHED-N-HETERYL)-1H-INDOLES

BACKGROUND OF THE INVENTION (a) Field of the Invention

This invention relates to 3-arylcarbonyl-1-(C-attached-N-heteryl)-1H-indoles which are useful as analgesic, antirheumatic, anti-inflammatory and antiglaucoma agents.

(b) Information Disclosure Statement

It is believed that compounds of the indole series having a nitrogen-containing heterocyclic group attached to the nitrogen atom of the indole either directly through a carbon atom of the heterocycle or through an intervening alkylene group attached to a carbon atom of the heterocycle and having, in addition, any carbonyl-containing function at the 3-position of the indole nucleus are unknown.

3-Arylcarbonyl substituted-1H-indoles having a nitrogen-containing heterocyclic group attached to the 1-position through the nitrogen atom of the heterocycle have been disclosed in the prior art, for example in Deschamps et al. U.S. Pat. No. 3,946,029, which describes compounds useful as fibrinolytic and anti-inflammatory agents, and in Bell U.S. Pat. No. 4,634,776, which discloses compounds useful as analgesic, antirheumatic and anti-inflammatory agents.

Essentially the same disclosure of Deschamps U.S. Pat. No. 3,946,029 is found in Inion et al., Europ. J. of Med. Chem., 10(3), 276–285 (1975). Specifically disclosed in both the Deschamps and Inion et al. references is 2-isopropyl-3-(3-pyridylcarbonyl)-1-[2-(4-morpholinyl)ethyl]indole.

Herbst U.S. Pat. No. 3,489,770 generically discloses compounds having the formula:

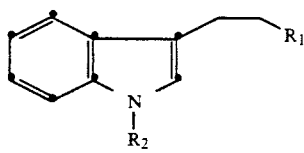

where, inter alia, $R_1$ is "diloweralkylamino, pyrrolidinyl, piperidino and morpholino and $R_2$ is . . . cyclo (lower) alkanoyl and adamantanyl carbonyl". Although not within the ambit of the above-defined genus, the Herbst patent also discloses a variety of species where $R_2$ is an arylcarbonyl group. Specifically disclosed, for example, is the species "1-p-(chlorobenzoyl)-3-(2-morpholinoethyl)indole". The compounds are said to possess anti-inflammatory, hypotensive, hypoglycemic and CNS activities.

Tambute, Acad. Sci. Comp. Rend., Ser. C, 278(20), 1239–1242 (1974) discloses compounds of the formula:

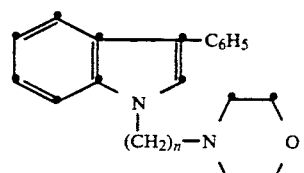

where n is 2 or 3. No utility for the compounds is given.

1-Primary amino-lower-alkyl-3-arylcarbonyl-1H-indoles for which no utility is stated are disclosed by Dalla Croce, Chem. Abst., 80, 95655f (1974).

The prior art also discloses a number of indoles having no substituent at the 3-position and a C-attached heterocyclic alkyl group attached to the 1-position. For example Bosch et al., J. Org. Chem., 48(25), 4836–41 (1983) disclose the species 1-[(1-methyl-4-piperidinyl)-methyl]-1H-indole; Bosch et al., Tetrahedron, 40(8), 1419–24 (1984) disclose 1-[(1-methyl-2-oxo-4-piperidyl)methyl]-1-indole and 1-](1-methyl-1,2,5,6-tetrahydro-4-pyridyl)methyl]-1H-indole; and Bennasar et al., Tetrahedron, 42(2), 637-647 (1986) disclose 1-[4-(3-methoxy-1-methyl-1,2,5,6-tetrahydropyridyl)-methyl]-1H-indole and 1-[4-(1-methyl-3-oxopiperidyl)methyl]-1H-indole, all useful as intermediates for the preparation of a partial structure of the indole alkaloid vinoxine.

Vartangan et al., Ann. Khim. Zh., 38(5), 308–313 (1985); Chem. Abst. 105, 114874e (1985) disclose compounds of the formula:

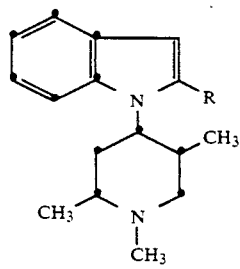

where R is hydrogen, COOH or COOCH$_3$. for which no utility is disclosed; Nilsson et al., Acta. Chem. Scand, Ser. B, B39(7), 531–537 (1985) disclose compounds having the formula:

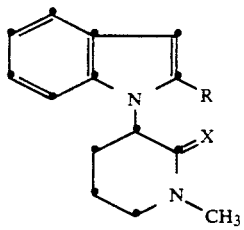

where X is 0 or S and R is hydrogen or methyl which were prepared for circular dichroism studies; and Sasakura et al., Syn. Comm. 18(3), 265–273 (1988) disclose compounds having the formula:

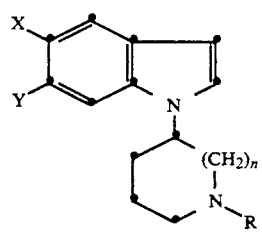

where X is hydrogen, chlorine, fluorine or methoxy; Y is hydrogen or fluorine; R is methyl or benzyl and n is 1 or 2 for which no utility is disclosed.

SUMMARY

In a composition of matter aspect, the invention relates to 2—$R_2$–$R_4$-substituted-3-arylcarbonyl-1-[(C-attached-N-aliphatic heteryl) (Alk)$_n$]-1H-indoles and their acid-addition salts which are useful as analgesic, antirheumatic, anti-inflammatory and antiglaucoma agents In a further composition aspect, the invention relates to 2-$R_2$–$R_4$-substituted-3-arylcarbonyl-1-[(C-attached-N-aromatic heteryl) (Alk)$_n$]-1H -indoles and the acid-addition salts and quaternary ammonium salts thereof, which are useful as intermediates for the preparation of said 2-$R_2$–$R_4$-substituted-3-arylcarbonyl-1-[(C-attached-N-aliphatic heteryl)(Alk)$_n$]-1H-indoles.

In a further composition aspect, the invention relates to 2-$R_2$–$R_4$-substituted-1-[(C-attached-N-aliphatic or aromatic heteryl)(Alk)$_n$]-1H-indoles, and acid-addition salts thereof, which are useful as intermediates for the preparation of said 2-$R_2$–$R_4$-substituted-3-arylcarbonyl-1-[(C-attached-N-aliphatic heteryl)(Alk)$_n$]-1H-indoles and 2-$R_2$–$R_4$-substituted-3-arylcarbonyl-1-[(C-attached-N-aromatic heteryl)(Alk)$_n$]-1H-indoles.

In a further composition aspect, the invention relates to 2-$R_2$–$R_4$-substituted-3-arylcarbonyl-1-lower-alkylsulfonyl- or 1-arylsulfonyl-1H-indoles, which are useful as intermediates for the preparation of said 2-$R_2$–$R_4$-substituted-1-[(C-attached-N-aliphatic heteryl)(Alk)$_n$]-1H-indoles.

In a further composition aspect, the invention relates to 2-$R_2$–$R_4$-substituted-3-arylcarbonyl-1-tri-lower-alkylsilylmethyl-1H-indoles, which are useful as intermediates for the preparation of said 2-$R_2$–$R_4$-substituted-1-[(C-attached-N-aliphatic heteryl) (Alk)$_n$]-1H-indoles.

In a further composition aspect, the invention relates to 2-$R_2$–$R_4$-substituted-3-phenylthio-1-[(C-attached-N-heteryl) (Alk)$_n$]-1H-indoles, which are useful as intermediates for the preparation of said 2-$R_2$–$R_4$-substituted-3-arylcarbonyl-1-[(C-attached-N-heteryl)(Alk)$_n$]-1H-indoles.

In a process aspect, the invention relates to a process for preparing said 2-$R_2$–$R_4$-substituted-3-arylcarbonyl-1-[(C-attached-N-heteryl)(Alk)$_n$]-1H-indoles, which comprises reacting a 2-$R_2$–$R_4$-substituted-1-[(C-attached-N-heteryl) (Alk)$_n$]-1H-indole with an arylcarboxylic acid halide in the presence of a Lewis acid In a second process aspect, the invention relates to a process for preparing 2-$R_2$–$R_4$-substituted-3-arylcarbonyl-1-[(C-attached-N-heteryl)(Alk)$_n$]-1H-indoles which comprises reacting a 2-$R_2$–$R_4$-substituted-3-arylcarbonylindole with a (C-attached-N-heteryl)-lower-alkyl halide or toluenesulfonate in the presence of an acid acceptor and optionally in the presence of a catalytic amount of an alkali metal iodide.

In a further process aspect, the invention relates to a process for preparing 2-$R_2$–$R_4$-substituted-3-arylcarbonyl-1-[(C-attached-N-heteryl)-lower-alkyl]-1H-indoles which comprises reacting a 2-$R_2$–$R_4$-substituted-3-arylcarbonyl-1-lower-alkylsulfonyl- or 1-arylsulfonyl-1H-indole with a (C-attached-N-heteryl)-lower-alkanol.

In a further process aspect, the invention relates to a process for preparing 2-$R_2$–$R_4$-substituted-3-arylcarbonyl-1-[(4-$R_6$-3-$R_5$-2-morpholinyl)methyl]-1H-indoles which comprises reacting a 1-halo-3-$R_5$-2,3-propylene oxide with a 2-$R_2$–$R_4$-substituted-indole in the presence of an acid acceptor; reacting the product with ammonia or a primary amine, $R_6NH_2$; reacting the product with a halo acetyl halide in the presence of base; reducing the resulting 2-$R_2$–R4-substituted-1-[(4-$R_6$-3-$R_5$-oxo-2-morpholinyl)methyl]-1H-indole and reacting the resulting 2-$R_2$–$R_4$-substituted-1-[(4-$R_6$-3-$R_5$-2-morpholinyl)-methyl]-1H-indole with an arylcarboxylic acid halide in the presence of a Lewis acid.

In a further process aspect, the invention relates to a process for preparing 2-$R_2$–$R_4$-substituted-3-arylcarbonyl-1-[(4-$R_6$-3- and/or 5-$R_5$-2-morpholinyl)methyl]-1H-indoles which comprises reacting a 1-halo-3-R -2,3-propylene oxide with a 2-$R_2$–$R_4$-substituted indole in the presence of an acid-acceptor; reacting the product with an appropriate N-$R_6$-2-$R_5$-ethanolamine; cyclizing the resulting 2-$R_2$–$R_4$-substituted-1-{k2-hydroxy-3-[N-(2-hydroxy-1-$R_5$-ethylamino)-3-$R_5$-3-N-$R_6$]propyl}-1H-indole with a di-lower-alkyl azodicarboxylate in the presence of triphenylphosphine or a trilower-alkylphosphine; and reacting the resulting 2-$R_2$–$R_4$-substituted-1-[(4-$R_6$-3- and/or 5-$R_5$-2-morpholinyl)methyl]-1H-indole with an aryl carboxylic acid halide in the presence of a Lewis acid.

In a further process aspect, the invention relates to a process for preparing 2-$R_2$–$R_4$-substituted-3-arylcarbonyl-1-(3-hydroxy-3-piperidinyl)- or (4-hydroxy-4-piperidinyl-1H-indoles which comprises reacting a 2-$R_2$–$R_4$-substituted- 3-arylcarbonyl-1-tri-lower-alkyl-silylmethyl-1H-indole with a 3- or 4-piperidinone, respectively, in the presence of an alkali metal fluoride.

In a method aspect, the invention relates to a method of use of said 2-$R_2$–$R_4$-substituted-3-arylcarbonyl-1-[(C-attached-N-aliphatic heteryl)(Alk)$_n$]-1H-indoles for the relief of pain or of rheumatic or inflammatory conditions.

In a composition aspect, the invention relates to compositions for the relief of pain or of rheumatic or inflammatory conditions which comprises administering to a patient in need of such relief an effective amount of said 2-$R_2$–$R_4$-substituted-3-arylcarbonyl-1-[(C-attached-N-aliphatic heteryl)-(Alk)$_n$]-1H-indoles. In a method aspect, the invention relates to a method for the treatment of glaucoma which comprises administering to a patient requiring such treatment an effective intraocular pressure reducing amount of a 2-$R_2$-3-arylcarbonyl-1-[(C-attached-N-aliphatic heteryl)(Alk)$_n$]-1H-indole or a pharmaceutically acceptable acid addition or lower-alkyl quaternary ammonium salt thereof. In a further composition aspect, the invention relates to compositions for the treatment of glaucoma which comprises a pharmaceutical carrier and an effective intraocular pressure reducing amount of a 2-$R_2$-3-arylcarbonyl-1-[(C-attached-N-aliphatic heteryl)(Alk)$_n$]-1H-indole or a pharmaceutically acceptable acid-addition or lower-alkyl quaternary ammonium salt thereof.

DETAILED DESCRIPTION OF THE PREFERRED EMBODIMENTS

More specifically, the invention relates to 2-$R_2$–$R_4$-substituted-3-arylcarbonyl-1-[(C-attached-N-heteryl) (Alk)$_n$]-1H-indoles, which are useful as analgesic, antirheumatic, anti-inflammatory and anti-glaucoma agents, having the formula:

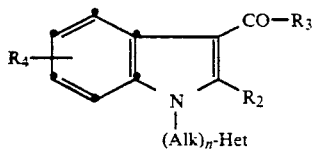

where:
- $R_2$ is hydrogen or lower-alkyl;
- $R_3$ is phenyl (or phenyl substituted by from one to two substituents selected from halogen, lower-alkoxy, hydroxy, lower-alkyl, nitro, amino, lower-alkylamino, di-lower-alkylamino, lower-alkylmercapto, lower-alkylsulfinyl, lower-alkylsulfonyl and methylenedioxy), 2- or 4-biphenyl or 1- or 2-naphthyl (or 1- or 2-naphthyl substituted by from one to two substituents selected from lower-alkyl, lower-alkoxy, halogen, lower-alkylmercapto, lower-alkylsulfinyl, lower-alkylsulfonyl and trifluoromethyl);
- $R_4$ is hydrogen or from one to two substituents selected from lower-alkyl, hydroxy, lower-alkoxy and halogen at the 4-, 5-, 6- or 7-positions;
- Alk is lower-alkylene containing from one to four carbon atoms which may contain a lower-alkyl group;
- Het is an aliphatic heterocycle selected from the group consisting of 2- or 3-pyrrolidinyl or 2- or 3-pyrrolidinyl substituted on any available ring carbon thereof by lower-alkyl), 2-, 3- or 4-piperidinyl (or 2-, 3- or 4-piperidinyl substituted on any available ring carbon atom thereof by lower-alkyl), 3-hydroxy-3-piperidinyl, 4-hydroxy-4-piperidinyl, 2- or 3-morpholinyl (or 2- or 3-morpholinyl substituted on any available ring carbon atom thereof by lower-alkyl), 2- or 3-thiomorpholinyl (or the S-oxides thereof or 2- or 3-thiomorpholinyl, or the S-oxides thereof, substituted on any available ring carbon atom thereof by lower-alkyl), 3-(1,2,5,6-tetrahydropyridinyl), 3-azetidinyl, 2-, 3- or 4-hexahydroazepinyl, 2,3,4,5,6,7-hexahydro-1,4-thiazepinyl, 2-piperazinyl and 2-indolinyl, where each of said Het groups may be either unsubstituted on the nitrogen atom (or atoms) thereof or substituted thereon by a lower-alkyl, benzyl, lower-alkoxybenzyl or benzhydryl group; and n is 0 or 1, except n is not 0 when the (Alk) moiety is attached to a ring carbon atom adjacent to a ring N, 0 or S atom of a Het group;

and acid-addition and lower-alkyl quaternary ammonium salts thereof.

Preferred compounds of Formula I above are those where:
- $R_2$ is hydrogen or lower-alkyl;
- $R_3$ is phenyl (or phenyl substituted by from one to two substituents selected from halogen, lower-alkoxy, hydroxy, lower-alkyl, nitro, amino, lower-alkylmercapto and lower-alkylsulfinyl) or 1-naphthyl;
- $R_4$ is hydrogen or from one to two substituents selected from lower-alkyl, hydroxy, lower-alkoxy and halogen at the 4-, 5-, 6- or 7-positions;
- Alk is lower-alkylene containing from one to four carbon atoms which may contain a lower-alkyl group; and
- Het is an aliphatic heterocycle selected from the group consisting of 2- or 3-pyrrolidinyl, 5-lower-alkyl-2- or 3-pyrrolidinyl, 5,5-di-lower-alkyl-2- or 3-pyrrolidinyl, 2-, 3- or 4-piperidinyl, 5-lower-alkyl-2-, 3- or 4-piperidinyl, 3-hydroxy-3-piperidinyl, 4-hydroxy-4-piperidinyl, 2- or 3-morpholinyl, 5-lower-alkyl-2-or 3-morpholinyl, 2-or -thiomorpholinyl (or the S-oxides thereof), 5-lower-alkyl-2- or 3-thiomorpholinyl, 3-(1,2,5,6-tetrahydropyridinyl), 3-azetidinyl, 2-, 3- or 4-hexahydroazepinyl, 2,3,4,5,6,7-hexahydro-1,4thiazepinyl, 2-piperazinyl and 2-indolinyl, where each of said Het groups may be either unsubstituted on the nitrogen atom (or atoms) thereof or substituted thereon by a lower-alkyl, benzyl, lower-alkoxybenzyl or benzhydryl group; and
- n is 0 or 1, except that n is not 0 when the (Alk) moiety is attached to a ring carbon atom adjacent to a ring N, O or S atom of a Het group.

Particularly preferred compounds of Formula I are those where:
- $R_2$ is hydrogen or lower-alkyl;
- $R_3$ is phenyl (or phenyl substituted by from one to two substituents selected from halogen, lower-alkoxy, hydroxy, lower-alkyl, nitro, amino, lower-alkylmercapto and lower-alkyl sulfinyl) or 1-naphthyl;
- $R_4$ is hydrogen or halogen at the 4-, 5-, 6- or 7-positions;
- Alk is either CHR', where R' is hydrogen or lower-alkyl, or Alk is $CH_2CH_2$;
- Het is 2- or 3-pyrrolidinyl, 5-lower-alkyl-2-pyrrolidinyl, 5,5-di-lower-alkyl-2- or 3-pyrrolidinyl, 2-, 3- or 4-piperidinyl, 4-hydroxy-4-piperidinyl, 2- or 3-morpholinyl, 2- or 3-thiomorpholinyl (or the S-oxides thereof), 3-(1,2,5,6-tetrahydropyridinyl), 3-azetidinyl, 3-hexahydroazepinyl, 2,3,4,5,6,7-hexahydro-1,4-thiazepinyl, 2-piperazinyl or 2-indolinyl, where each of said Het groups may be either unsubstituted on the nitrogen atom (or atoms) thereof or substituted thereon by a lower-alkyl, benzyl, lower-alkoxybenzyl or benzhydryl group; and
- n is 0 or 1, except that n is not 0 when the (Alk) moiety is attached to a ring carbon atom adjacent to a ring N, 0 or S atom of a Het group.

Especially preferred compounds of Formula I above are those where:
- $R_2$ is hydrogen or lower-alkyl;
- $R_3$ is lower-alkoxyphenyl or 1-naphthyl;
- $R_4$ is hydrogen or 5-fluoro;
- Alk is either CHR', where R' is hydrogen or lower-alkyl, or Alk is $CH_2CH_2$;
- Het is N-lower-alkyl-2- or 3-pyrrolidinyl, N-lower-alkyl-5-lower-alkyl-2- or 3-pyrrolidinyl, N-lower-alkyl-2- or 3-piperidinyl, 4-lower-alkyl-2-morpholinyl, 4-lower-alkyl-2- or 3-thiomorpholinyl, or the S-oxides thereof, or 2-piperazinyl; and
- n is 0 or 1, except that n is not 0 when the (Alk) moiety is attached to a ring carbon atom adjacent to a ring N, 0 or S atom of a Het group.

Also contemplated by the invention are compounds of Formula I above where:
- $R_2$ is hydrogen or lower-alkyl;
- $R_3$ is phenyl (or phenyl substituted by from one to two substituents selected from halogen, lower-alkoxy, hydroxy, lower-alkyl, nitro, amino, lower-alkyl-amino, di-lower-alkylamino, lower-alkylmercapto, lower-alkylsulfinyl, lower-alkylsulfonyl and methylenedioxy), 2- or 4-biphenyl or 1- or 2-naphthyl (or 1- or 2-naphthyl substituted by from one to two substituents selected from lower-alkyl, lower-alkoxy, halogen, lower-alkylmercapto, lower-alkylsulfinyl, lower-alkylsulfonyl and trifluoromethyl);

$R_4$ is hydrogen or from one to two substituents selected from lower-alkyl, hydroxy, lower-alkoxy and halogen at the 4-, 5-, 6- or 7-positions;

Alk is lower-alkylene containing from one to four carbon atoms which may contain a lower-alkyl group;

Het is an aromatic heterocycle selected from the group consisting of 2- or 3-pyrrolyl, 5-lower-alkyl-2- or 3-pyrrolyl, 2-, 3- or 4-pyridinyl and 2-pyrazinyl, where each of said 2- or 3-pyrrolyl or 5-lower-alkyl-2- or 3-pyrrolyl may be either unsubstituted or substituted on the nitrogen atom thereof by a lower-alkyl, benzyl or benzhydryl group, or the acid-addition salts and lower-alkyl, benzyl, 4-lower-alkoxybenzyl or benzhydryl quaternary ammonium salts of basic members thereof; and n is 0 or 1, except that n is not 0 when the (Alk) moiety is attached to a ring carbon atom adjacent to a ring N atom of a Het group.

Also within the purview of the present invention are compounds, useful as intermediates for the preparation of compounds of Formula I, having the Formula II:

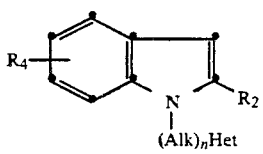

where:

$R_2$ is hydrogen or lower-alkyl;

$R_4$ is hydrogen or from one to two substituents selected from lower-alkyl, hydroxy, lower-alkoxy and halogen at the 4-, 5-, 6- or 7-positions;

Alk is lower-alkylene containing from one to four carbon atoms which may contain a lower-alkyl group;

Het is an aliphatic heterocycle selected from the group consisting of 2- or 3-pyrrolidinyl, 5-oxo-2- or 3-pyrrolidinyl (or 2- or 3-pyrrolidinyl or 5-oxo-2- or 3-pyrrolidinyl substituted on any available ring carbon atom thereof by lower-alkyl), 2-, 3- or 4-piperidinyl (or 2-, 3- or 4-piperidinyl substituted on any available carbon atom by lower-alkyl), 3-hydroxy-3-piperidinyl, 4-hydroxy-4-piperidinyl, 2-or or 3-morpholinyl, 5-oxo-2- or 3-morpholinyl (or 2-or 3-morpholinyl or 5-oxo-2- or 3-morpholinyl substituted on any available carbon atom thereof by lower-alkyl), 2- or 3-thiomorpholinyl. (or the S-oxides thereof, or 2- or 3-thiomorpholinyl, or the S-oxides thereof, substituted on any available ring carbon atom thereof by lower-alkyl), 3-(1,2,5,6-tetrahydropyridinyl), 3-azetidinyl, 2-, 3- or 4-hexahydroazepinyl, 2,3,4,-5,6,7-hexahydro-1,4-thiazepinyl, 2-piperazinyl or 2-indolinyl, or an aromatic heterocycle selected from the group consisting of 2- or 3-pyrrolyl (or 2-or 3-pyrrolyl substituted on any available carbon atom thereof by lower-alkyl), 2-, 3- or 4-pyridinyl and 2-pyrazinyl, where each of said aliphatic Het groups or said 2- or 3-pyrrolyl (or lower-alkyl substituted-2- or 3-pyrrolyl groups) may be either unsubstituted on the nitrogen atom (or atoms) thereof or substituted thereon by a lower-alkyl, benzyl, lower-alkoxybenzyl or benzhydryl group; and n is 0 or 1, except that n is not 0 when the (Alk) moiety is attached to a ring carbon atom adjacent to a ring N, 0 or S atom of a Het group; and (B) acid-addition salts of basic members thereof.

Also within the purview of the present invention are compounds, useful as intermediates for the preparation of the compounds of Formula I, having the formula:

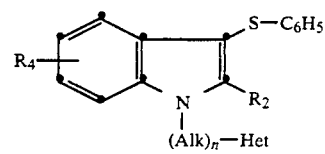

where:

$R_2$ is hydrogen or lower-alkyl;

$R_4$ is hydrogen or from one to two substituents selected from lower-alkyl, hydroxy, lower-alkoxy and halogen at the 4-, 5-, 6- or 7-positions;

Alk is lower-alkylene containing from one to four carbon atoms which may contain a lower-alkyl group;

Het is an aliphatic heterocycle selected from the group consisting of 2- or 3-pyrrolidinyl (or 2- or 3-pyrrolidinyl substituted on any available ring carbon thereof by lower-alkyl), 2-, 3- or 4-piperidinyl (or 2-, 3- or 4-piperidinyl substituted on any available ring carbon atom by lower-alkyl), 3-hydroxy-3 piperidinyl, 4-hydroxy-4-piperidinyl, 2or 3-morpholinyl (or 2-or 3-morpholinyl substituted on any available carbon atom by lower-alkyl), 2- or 3-thiomorpholinyl (or the S-oxides thereof, or 2- or 3-thiomorpholinyl, or the S-oxides thereof, substituted on any available ring carbon atom thereof by lower-alkyl), 3-(1,2,5,6-tetrahydropyridinyl), 3-azetidinyl, 2-, 3- or 4-hexahydroazepinyl, 2,3,4,-5,6,7-hexahydro-1,4-thiazepinyl, 2-piperazinyl and 2-indolinyl, where each of said Het groups may be either unsubstituted on the nitrogen atom (or atoms) thereof or substituted thereon by a lower-alkyl, benzyl, lower-alkoxybenzyl or benzhydryl group; and n is 0 or 1, except that n is not 0 when the Alk moiety is attached to a ring carbon atom adjacent to a ring N, 0 or S atom of a Het group; and (B) acid-addition salts thereof.

Also within the purview of the present invention are compounds, useful as intermediates for the preparation of the compounds of Formula I, having the Formula VII:

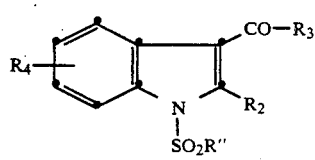

where:

$R_2$ is hydrogen or lower-alkyl;

$R_3$ is phenyl (or phenyl substituted by from one to two substituents selected from halogen, lower-alkoxy, hydroxy, lower-alkyl, nitro, amino, lower-alkylamino, di-lower-alkylamino, lower-alkylmercapto, lower-alkylsulfinyl, lower-alkylsulfonyl and methylenedioxy), 2- or 4-biphenyl or 1- or 2-naphthyl (or 1- or 2-naphthyl substituted by from one to two substituents selected from lower-alkyl, lower-alkoxy, halogen, lower-alkylmercapto, lower-alkylsulfinyl, lower-alkylsulfonyl and trifluoromethyl);

$R_4$ is hydrogen or from one to two substituents selected from lower-alkyl, hydroxy, lower-alkoxy or halogen at the 4-, 5-, 6- or 7-positions; and R" is lower-alkyl or aryl such as phenyl or lower-alkyl-substituted-phenyl.

Also within the purview of the present invention are compounds, useful as intermediates for the preparation of the compounds of Formula I, having the formula IX:

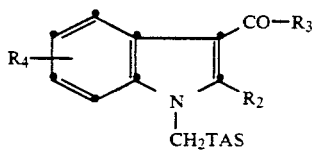

where:

$R_2$ is hydrogen or lower-alkyl;

$R_3$ is phenyl (or phenyl substituted by from one to two substituents selected from halogen, lower-alkoxy, hydroxy, lower-alkyl, nitro, amino, lower-alkylamino, di-lower-alkylamino, lower-alkylmercapto, lower-alkylsulfinyl, lower-alkylsulfonyl and methylenedioxy), 2- or 4-biphenyl or 1- or 2-naphthyl (or 1- or 2-naphthyl substituted by from one to two substituents selected from lower-alkyl, lower-alkoxy, halogen, lower-alkylmercapto, lower-alkylsulfinyl, lower-alkylsulfonyl and trifluoromethyl);

$R_4$ is hydrogen or from one to two substituents selected from lower-alkyl, hydroxy, lower-alkoxy and halogen at the 4-, 5-, 6- or 7-positions; and TAS is a tri-lower-alkylsilyl group.

Also within the purview of the present invention are compounds within the ambit of Formula I above, which are useful

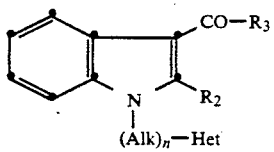

where:

$R_2$ is hydrogen or lower-alkyl;

$R_3$ is phenyl (or phenyl substituted by halogen, lower-alkoxy, hydroxy, lower-alkyl or lower-alkylmercapto) or 1-naphthyl;

Alk is lower-alkylene containing from one to four carbon atoms which may contain a lower-alkyl group;

Het is 2- or 3-pyrrolidinyl, 5-lower-alkyl-2-pyrrolidinyl, 5,5-di-lower-alkyl-2-pyrrolidinyl, 2-, 3- or 4-piperidinyl, 2- or 3-morpholinyl, 3-azetidinyl, 3-hexahydroazepinyl or 2-piperazinyl, where each of said Het groups may be either unsubstituted on the nitrogen atom (or atoms) thereof or substituted thereon by a lower-alkyl or benzyl group;

n is 0 or 1, except that n is not 1 when the Alk moiety is attached to a ring carbon atom adjacent to a ring N, 0 or S atom of a Het group; and pharmaceutically acceptable acid-addition and lower-alkyl quaternary ammonium salts thereof.

As used herein, unless specifically defined otherwise, the terms lower-alkyl and lower-alkoxy mean monovalent aliphatic radicals, including branched chain radicals, of from one to four carbon atoms, for example methyl, ethyl, propyl, isopropyl, butyl, sec.-butyl, methoxy, ethoxy, propoxy, isopropoxy, butoxy and sec.-butoxy.

As used herein the terms halo or halogen mean fluorine, chlorine or bromine.

As used herein the terms C-attached-N-heteryl and C-attached-N-heterocycle mean a nitrogen-containing heterocycle, as more precisely defined herein, which is attached through a ring carbon atom thereof to the nitrogen atom of the indole nucleus either directly through a single bond or through an alkylene group, Alk, where Alk is defined as above.

In one method, the compounds of Formula I are prepared by reaction of a 2-$R_2$-$R_4$-substituted-1-[(C-attached-N-heteryl) (Alk)$_n$]-1H-indole with an appropriate arylcarboxylic acid halide ($R_3$CO—X) in the presence of a Lewis acid, such as aluminum chloride, and in an organic solvent inert under the conditions of the reaction. Suitable solvents are chlorinated hydrocarbons, such as methylene dichloride (hereinafter MDC) or ethylene dichloride (hereinafter EDC). The reaction is carried out at a temperature from 0° C. up to the boiling point of the solvent used. The method is illustrated by the reaction:

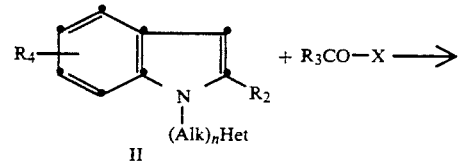

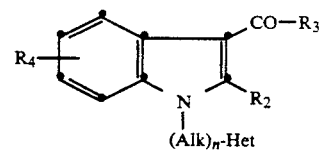

where $R_2$, $R_3$, $R_4$, Alk, Het and n have the meanings given above for Formula II and X is halogen.

The intermediate 2-$R_2$-$R_4$-substituted-1-[(C-attached-N-heteryl) (Alk)$_n$]-1H-indoles of Formula II are prepared by one of several methods. In one method an appropriate indole of Formula III is reacted with an appropriate C-attached-[halo-(Alk)n]-N-heterocycle of Formula V in the presence of an acid acceptor and in an organic solvent inert under the conditions of the reaction as represented by the equation:

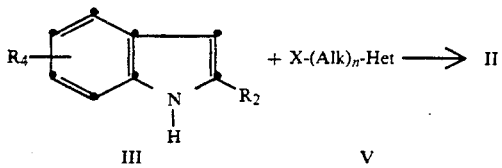

where $R_2$, $R_4$, Alk, Het, n and X have the meanings given above for Formula II. Suitable acid acceptors are alkali metal carbonates or hydroxides, and suitable solvents are lower-alkanols, acetone, dimethylformamide (hereinafter DMF) or dimethylsulfoxide (hereinafter DMSO). The reaction is carried out at a temperature between ambient temperature and the boiling point of the solvent.

A second method for the preparation of the intermediates of Formula II involves preparation of a 2-$R_2$-$R_4$-substituted-3-phenylmercapto-1-[(C-attached-N-heteryl) (Alk)$_n$]-1H-indole by cyclization of an N-[(C-attached-N-heteryl)-(Alk)n]phenylhydrazine of Formula IV with phenylmercapto acetaldehyde ($R_2$ is hydrogen) or with a phenylmercaptomethyl lower-alkyl ketone ($R_2$ is lower-alkyl) by heating the reactants in glacial acetic acid followed by catalytic cleavage of the phenylmercapto group from the resulting product, preferably by heating the latter in the presence of Raney nickel in a refluxing lower-alkanol, such as ethyl alcohol. The intermediate N-[(C-attached-N-heteryl)(Alk)]-phenylhydrazine in turn is prepared by nitrosation of an appropriate N-[(C-attached-N-heteryl)(Alk)$_n$]phenylamine with sodium nitrite in dilute mineral acid, for example dilute hydrochloric acid, and reduction of the resulting N-nitroso-N-[ (C-attached-N-heteryl)(Alk)$_n$]-phenylamine with an alkali metal aluminum hydride in an inert organic solvent, for example tetrahydrofuran (hereinafter THF), diethyl ether or dibutyl ether. The method is illustrated by the reaction sequence:

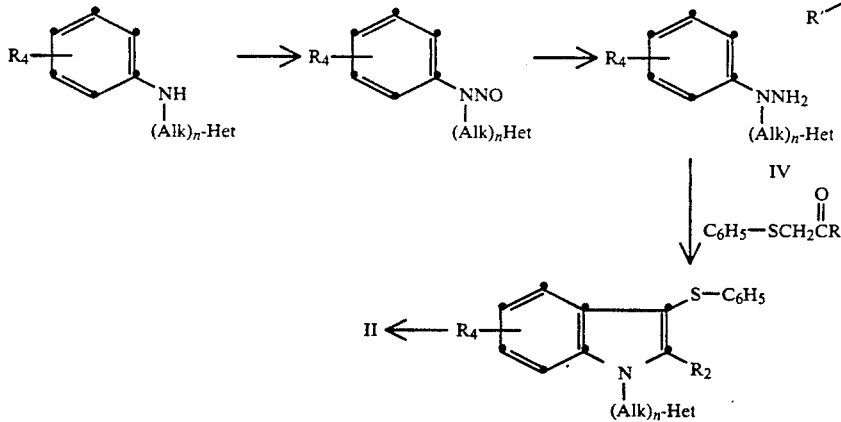

where $R_2$, $R_4$, Alk, Het and n have the meanings given above for Formula II.

The intermediate 2-$R_2$-$R_4$-substituted-3-phenylmercapto-1-[(C-attached-N-heteryl)-(Alk)$_n$]-1H-indole used in the synthetic approach described above can also be prepared via the Grignard reaction by reaction of a lower-alkyl magnesium halide with an appropriate 2-$R_2$-$R_4$-substituted-indole of Formula II and reaction of the resulting Grignard compound with diphenyldisulfide. The reaction is carried out at a temperature from 0° to 20° C. and in an inert organic solvent such as diethyl ether, THF or dioxane.

The compounds of Formula II where Het is 2-morpholinyl or 3-lower-alkyl-2-morpholinyl and n is 1 are prepared by one of two methods. In the first method an appropriate indole is reacted with a 1-halo-3-$R_5$-2,3-propyleneoxide, i.e. a halohydrin, in the presence of a base, such as an alkali metal carbonate or hydroxide, and the resulting 2-$R_2$-$R_4$-substituted-1-(3-$R_5$-2,3-epoxy-1-propyl)-1H-indole is reacted either with ammonia or a lower-alkylamine, $R_6NH_2$, in an organic solvent. Suitable solvents for both reactions are DMF, DMSO or THF, and the reaction is carried out at temperatures from about ambient temperature to the boiling point of the solvent used. The resulting 2-$R_2$-1-(3-amino-3-$R_5$-2-hydroxypropyl)-1H-indole is then reacted with a halo acetyl halide in the presence of a base, such as a tri-lower-alkylamine, in an inert organic solvent, such as MDC, diethyl ether or THF at a temperature from −70° C. to ambient temperature, and the product, 2-$R_2$-$R_4$-substituted-1-[(4-$R_6$-5-oxo-3-$R_5$-2-morpholinyl)methyl]-1H-indole, is reduced with borane THF in a suitable organic solvent, for example THF, diethyl ether or dibutyl ether, at a temperature from ambient temperature up to about the boiling point of the solvent used. The method is illustrated by the following reaction sequence:

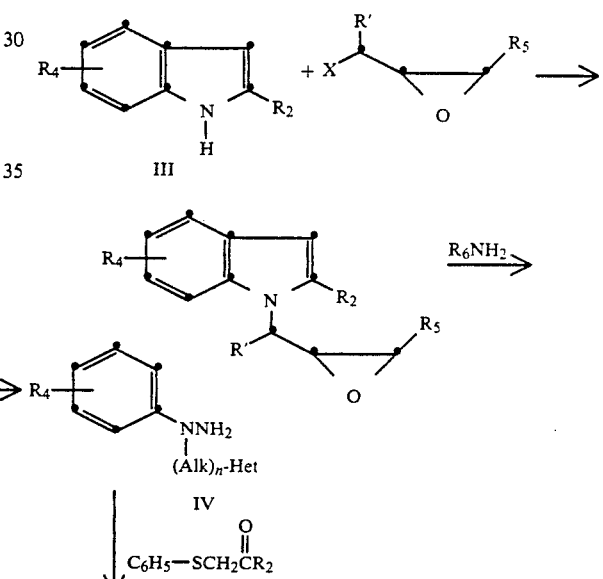

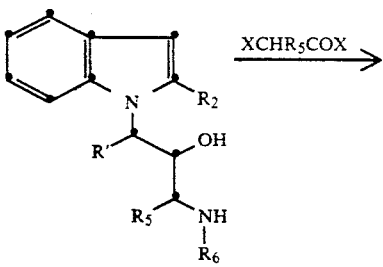

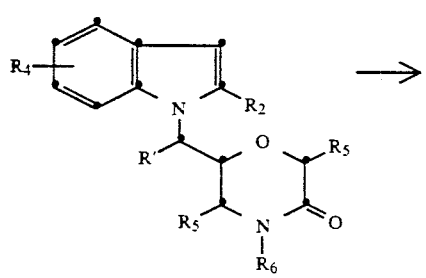

where R₂ and R₄ have the meanings given above and R', R₅ and R₆ are each hydrogen or lower-alkyl.

As indicated by the reaction sequence, this method affords a means of preparing compounds of Formula II where Het is 2-morpholinyl with a lower-alkyl group in either or both of the 3- and 6-positions.

A method for the preparation of compounds of Formula II where Het is 2-morpholinyl with a lower-alkyl group in either or both of the 3- and 5-positions involves reaction of a 2-R₂-R₄-1-(3-R₅-2,3-epoxy-1-propyl)-1H-indole prepared as described above with a 2-(N-R₆)-2-R₅-ethanolamine and reaction of the resulting 2-R₂-R₄-substituted-1-{2-hydroxy-3-[N-( 2-hydroxy-1-R₅- ethylamino)-3-R₅-3-N-R₆]propyl}-1H-indole with a di-lower-alkyl azodicarboxylate in the presence of triphenylphosphine or a tri-lower-alkylphosphine to produce the desired product of Formula II. The cyclization reaction is carried out in an organic solvent inert under the conditions of the reaction, for example MDC, EDC or THF, and is usually exothermic and requires cooling with an external ice bath. The method is illustrated by the reaction sequence:

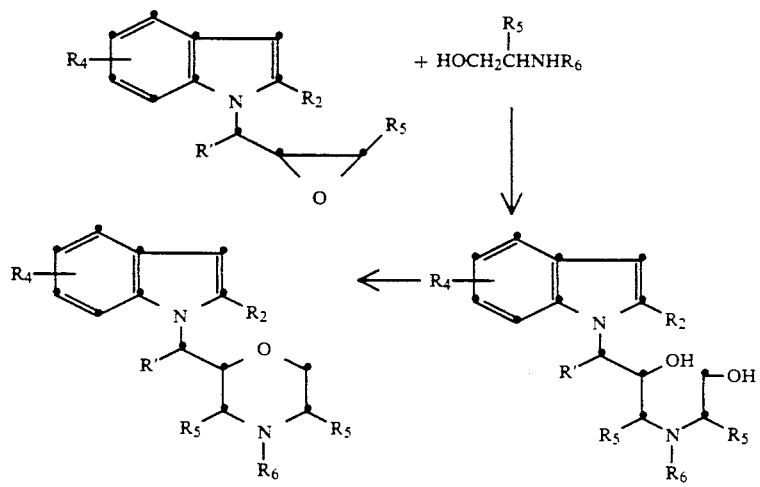

where R', R₂, R₄, R₅ and R₆ have the meanings given above.

Another approach to the preparation of the final products of Formula I comprises reaction of a 2-R₂-R₄-substituted-3-arylcarbonylindole of Formula VI with an appropriate C-attached-[X'-(Alk)ₙ]-N-heterocycle of Formula V using the same conditions described above for the first described method for preparation of the compounds of Formula II. The method is illustrated by the following reaction sequence:

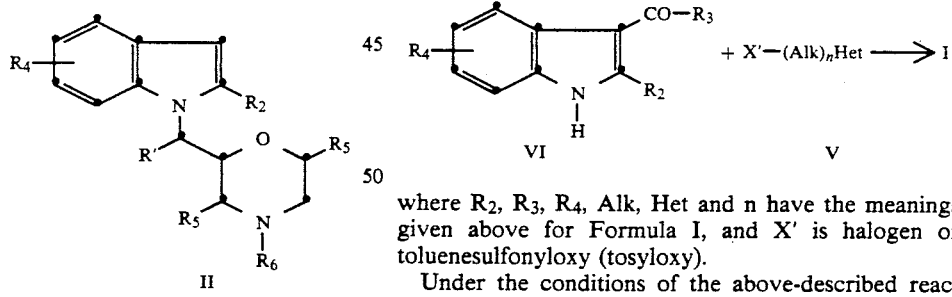

where R₂, R₃, R₄, Alk, Het and n have the meanings given above for Formula I, and X' is halogen or toluenesulfonyloxy (tosyloxy).

Under the conditions of the above-described reaction, the halo or tosyloxy (Alk)n-N-heterocycle sometimes undergoes rearrangement resulting in either ring expansion or ring contraction of the heterocyclic ring. In such cases, the product isolated may consist entirely of the rearranged product or a mixture of the latter and the expected unrearranged product thus necessitating separation of the products by conventional purification procedures such as fractional crystallization or chromatography. For example, we have found that use of 1-methyl-2-chloromethylpiperidine as the alkylating agent results in the formation of compounds where the piperidinylmethyl group undergoes ring expansion to the 1-methyl-3-azepinyl group. On the other hand, in our experience, use of either 1-methyl-3-tosyloxypiperidine or 1-ethyl-3-chloropiperidine as the alkylating agents produces, as the principal products, the compounds where the piperidine ring has undergone ring contraction to the 1-methyl-2-pyrrolidinylmethyl and the 1-ethyl-2-pyrrolidinylmethyl groups, respectively.

Another method for preparing the final products of Formula I comprises reacting a 2-$R_2$-$R_4$-substituted-3-$R_3$-arylcarbonyl-1-lower-alkylsulfonyl- or 1-arylsulfonyl-1H-indole of Formula VII with a hydroxy-(Alk)$_n$-N-heterocycle of Formula VIII in the presence of a strong base, for example sodium or potassium hydride or potassium or cesium carbonate in an anhydrous, organic solvent inert under the conditions of the reaction, for example toluene, dioxane, acetonitrile, THF, DMF or DMSO, at temperatures from ambient up to the boiling point of the solvent, in accordance with the equation:

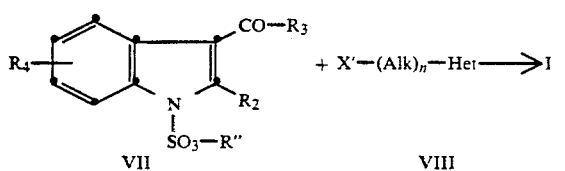

where $R_2$, $R_3$, $R_4$, Alk, Het and n have the meanings given above for Formula I and R" is lower-alkyl or aryl. The method is particularly adaptable to preparation of compounds where the group Het is 2- or 3-thiomorpholinyl, 5-lower-alkyl-2- or 3-thiomorpholinyl or 3-morpholinyl. The starting materials of Formula VII are prepared by reacting an appropriate 2-$R_2$-$R_4$-substituted-3-arylcarbonyl indole of Formula VI with a lower-alkylsulfonyl halide or an arylsulfonyl halide in the presence of a strong base, such as concentrated aqueous alkali and a tetra-lower-alkylammonium salt, such as tetrabutylammonium sulfate, in an organic solvent inert under the conditions of the reaction, such as MDC, EDC, THF, DMF or DMSO.

Still another method for preparing the compounds of Formula I where Het is a 2- or 3-pyrrolidinyl or 5-lower-alkyl-2- or 3-pyrrolidinyl group, a 2-, 3- or 4-piperidinyl group or a 2-piperazinyl group substituted on the nitrogen atom or atoms thereof by a lower-alkyl group (and which obviates the problem of the rearrangement of the piperidine ring using the N-alkylation procedure described above) comprises reducing catalytically a compound of Formula I where Het is 2- or 3-pyrrolyl or 5-lower-alkyl-2- or 3-pyrrolyl or a corresponding lower-alkyl quaternary ammonium salt of a compound where Het is 2-, 3- or 4-pyridinyl or 2-pyrazinyl in an organic solvent inert under the conditions of the reaction, for example lower-alkanols such as methyl alcohol or ethyl alcohol. A suitable catalyst is platinum oxide, and the reaction is preferably carried out in the presence of a mineral acid or in glacial acetic acid as a solvent.

The compounds of Formula I where Het is 3-hydroxy-3-piperidinyl or 4-hydroxy-4-piperidinyl or such groups substituted on the nitrogen atom by lower-alkyl, benzyl or benzhydryl, Alk is methylene and n is 1 are prepared by reacting a 2-$R_2$-$R_4$-substituted-3-arylcarbonyl indole of Formula VI with a halo-methyl tri-lower-alkyl silane in the presence of a strong base and in an organic solvent inert under the conditions of the reaction, such as DMF, THF or dioxane, and reaction of the resulting 2-$R_2$-$R_4$-substituted-3-arylcarbonyl-1-tri-lower-alkylsilylmethyl-1H-indole of Formula IX with an appropriate 1-$R_7$-3- or 1-$R_7$-4-piperidone in the presence of an alkali metal fluoride in an inert organic solvent. A preferred solvent is diethyleneglycol dimethyl ether (diglyme). The method is illustrated by the following reaction sequence for the preparation of compounds where the group Het is 1-$R_7$-4-hydroxy-4-piperidinyl, and chloromethyl trimethylsilane is used as the halomethyl tri-lower-alkyl silane:

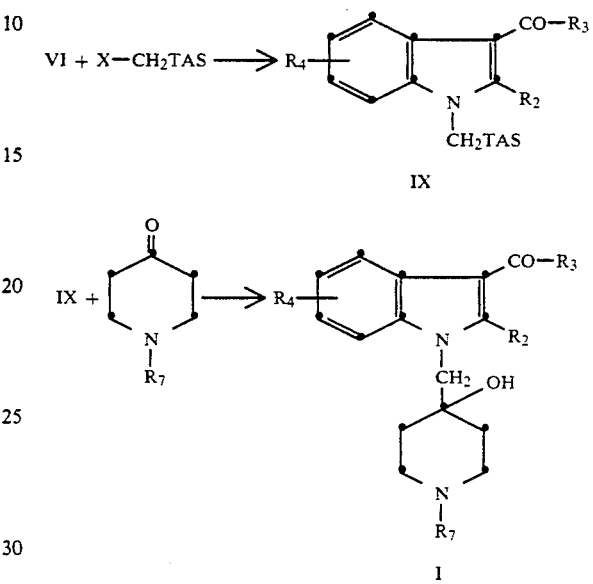

where $R_2$, $R_3$ and $R_4$ have the meanings given above, $R_7$ represents lower-alkyl, benzyl or benzhydryl, and TAS represents a tri-lower-alkylsilyl group.

Other compounds of Formula I within the ambit of the invention can be prepared by conventional chemical transformations of functional groups to prepare compounds with different functional groups. Such transformations, which are well known to those skilled in the art, include the oxidation of divalent sulfur-containing compounds, for example compounds containing lower-alkylmercapto or thiomorpholinyl groups, with hydrogen peroxide or with organic peracids such as performic, peracetic or o-chloroperbenzoic acids, to produce the corresponding sulfoxide or sulfone; catalytic reduction with hydrogen over a suitable catalyst, such as palladium-on-charcoal, of compounds containing a benzyl or a benzhydryl group on a nitrogen atom to effect debenzylation or debenzhydrylation; the catalytic reduction of a nitro group to prepare the corresponding amino compound or the reductive alkylation of secondary amine functions with an appropriate aldehyde to prepare the corresponding N-substituted compounds, such as N-lower-alkyl piperazinyl substituted compounds.

The intermediate 2-$R_2$-$R_4$-substituted indoles of Formula III and the 2-$R_2$-$R_4$-substituted-3-arylcarbonyl indoles of Formula VI are generally known compounds, being disclosed, for example, in U.S. Pat. No. 4,634,776. Buu Hoi et al., J. Am. Chem. Soc., 79, 625-628 (1957) also disclose 3-(1-naphthylcarbonyl)indole of Formula VI ($R_2$ and $R_4$ are hydrogen and $R_3$ is 1-naphthyl).

The intermediates of Formulas V and VIII useful for the preparation of compounds within the ambit of the invention are also generally known in the prior art, compounds of Formula V where X is chloro being disclosed, for example, by Blicke U.S. Pat. No. 2,965,301; German Patent 1,156,079; Feldkamp U.S. Pat. No. 2,826,588; British Patent 815,844; Taguchi et al., Chem. Pharm. Bull. (Tokyo) 13(3), 241–247 (1965); Feldkamp et al., J. Am. Chem. Soc., 74, 3831–3833 (1952); Henecka et al., Angew. Chem., 72, 960–963 (1960); Paul, Compt. rendu, 221(15), 412–414 (1945); Jucker et al., Helv. Chim. Acta, 45, 2383–2402 (1962); Norton et al., J. Am. Chem. Soc., 68, 1572–1576 (1946); and Balsamo et al., J. Med. Chem., 30(1), 222–225 (1987), and a species of Formula V where X is p-tosyloxy is disclosed by Anderson, J. Org. Chem., 37(24), 3953–3955 (1972). Intermediates of Formula VIII useful for the preparation of compounds within the ambit of the invention are disclosed, for example, by Blicke U.S. Pat. No. 2,965,301; Blicke et al., J. Am. Chem. Soc., 77, 29–31 (1955); and Eremeev et al., Khim. Geterosikl. Soedin, 9, 1280–1285 (1986) [Chem. Abs. 106, 176297y (1987)].

It will be appreciated that the compounds of the invention can have several chiral centers, for example, in the Alk group separating the indole and the C-attached-N-heteryl group when the Alk group is substituted by a lower-alkyl group on the carbon atom adjacent the indole nitrogen atom and at the carbon atom of the N-heteryl group to which the Alk function is attached and at any carbon atom of the N-heteryl group having an attached lower-alkyl group, $R_5$. The compounds thus can exist as optically active stereoisomers. All such stereoisomers are considered to be within the purview of the present invention, and if desired the isolation of the product of a particular stereochemical form, such as salts formed from optically active acids, can be accomplished by application of general principles well known in the art.

Due to the presence of at least one basic amino group in the C-attached-N-heteryl group, the compounds of Formula I can form acid-addition salts with acids. The compounds of Formula I in free base form are converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the novel bases and all of their acid-addition salts are readily interconvertible.

It will thus be appreciated that Formula I not only represents the structural configuration of the bases of Formula I but is also representative of the structural entity which is common to all of the compounds of Formula I, whether in the form of the free base or in the form of the acid-addition salts of the base. It has been found that, by virtue of these common structural entities the bases of Formula I and their acid-addition salts have inherent pharmacological activity of a type to be more fully described hereinbelow. This inherent pharmacological activity can be enjoyed in useful form for pharmaceutical purposes by employing the free bases themselves or the acid addition salts formed from pharmaceutically acceptable acids, that is acids whose anions are innocuous to the animal organism in effective doses of the salts so that beneficial properties inherent in the common structural entity represented by the free bases are not vitiated by side effects ascribable to the anions.

In utilizing this pharmacological activity of the salts of the invention, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base as explained above, or alternatively they can be converted to any desired pharmaceutically acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically acceptable free bases by reaction of the salts with aqueous base, or alternatively they can be converted to a pharmaceutically acceptable acid-addition salt by, for example, ion-exchange procedures.

The novel feature of the compounds of the invention, then, resides in the concept of the bases and cationic forms of the new 2-$R_2$-$R_4$-substituted-3-arylcarbonyl-1-[(C-attached-N-heteryl) (Alk)$_n$]-1H-indoles of Formula I and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride and the like.

The acid-addition salts are prepared by reacting the free base and the acid in an organic solvent and isolating the salt directly or by concentration of the solution.

In standard pharmacological test procedures, the compounds of Formula I have been found to possess analgesic, antirheumatic, anti-inflammatory and anti-glaucoma activities and are thus useful as analgesic, antirheumatic, anti-inflammatory and anti-glaucoma agents. In addition to the utility of the compounds of Formula III as intermediates in the preparation of compounds of Formula I, certain of the compounds of Formula III have been found to possess analgesic and anti-rheumatic activity, thus indicating usefulness of those species as anti-rheumatic and analgesic agents.

The test procedures used to determine the analgesic activities of the compounds have been described in detail in the prior art and are as follows: The acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exptl. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); and the Randall-Selitto analgesic test described by Randall and Selitto, Arch. Int. Pharmacodyn., 111, 409–419 (1957).

Antirheumatic and anti-inflammatory activities of the compounds of the invention were determined using the developing adjuvant arthritis assay in rats and the plasma fibronectin assay in arthritic rats. The developing adjuvant arthritis assay was used in conjunction with the plasma fibronectin assay as a primary screening method in the evaluation of compounds for potential use as disease modifying anti-rheumatic drugs. The procedure used to induce arthritis in rats is a modification of the methods published by Pearson, J. Chron. Dis. 16, 863–874 (1973) and by Glenn et al., Amer. J. Vet. Res. 1180–1193 (1965). Adjuvant induced arthritis bears many of the traits of rheumatoid arthritis. It is a chronic, progressive, deforming arthritis of the peripheral joints, with a primary mononuclear cell response consisting of bone and joint space invasion by pannus. In order to detect disease modifying anti-rheumatic drug activity, drug treatment is started before the disease has become irrevocably established. Since such drugs are not designed to be administered prophylactically, drug treatment of adjuvant arthritis is initiated at a time when the disease is developing but is not yet irreversible. Animals develop significant systemic arthritic disease which can be measured by swelling of the non-injected rear paw (NIP) 15 to 20 days following an initial injection on day 1 of complete Freund's adjuvant into the right hindfoot paw.

The important role played by fibronectin in arthritis has been evidenced by clinical [Scott et al., Ann. Rheum. Dis. 40, 142 (1981)]as well as experimental [Weissmann, J. Lab. Clin. Med. 100, 322 (1982)]studies. Plasma fibronectin measurements are made using the technique of rocket immuno-electrophoresis. Fibronectin levels in the arthritic rat are significantly higher than in normal animals. Nonsteroidal, anti-inflammatory drugs have no influence on the enhanced fibronectin levels seen in arthritic rats, while disease modifying anti-rheumatic drugs cause a significant decrease in plasma fibronectin.

It has been shown previously that smoking marijuana reduces intraocular pressure in man [Helper and Frank, Marijuana Smoking and Intraocular Pressure., J. Am. Med. Assoc. 217, 1392 (1971)]. Topical application or systemic injection of delta-9 tetrahydrocannabinol, a principal active ingredient in marijuana, also reduces intraocular pressure [Purnell and Gregg, delta-9 Tetrahydrocannabinol, Euphoria and Intraocular Pressure in Man., Ann. Opth. 7, 921–923 (1975); Green and Pederson, Effect of delta-9 Tetrahydrocannabinol on Aqueous Dynamics and Ciliary Body Permeability in the Rabbit Eye., Exptl. Eye Research 15, 499–507 (1973); Colasanti, Craig and Allara, Intraocular Pressure, Ocular Toxicity and Neurotoxicity after Administration of Cannabinol or Cannibigerol, Exptl. Eye Research 39, 252–259 (1984)]. Similarly, synthetic cannabinoids also reduce intraocular pressure [Green, Symunds, Oliver and Elijah, Intraocular Pressure Following Systemic Administration of Cannabinoids., Curr. Eye Research 2, 247–253 (1982); Tiedeman, Shields, Weber, Crow, Coccetto, Harris and Howes, Opthalmology, 88, 270–277 (1981); Colasanti et al., supra]. Cannabinoid receptor binding sites can be defined as those to which radio-labelled 4-(1,1-dimethylheptyl)-2,3'-dihydroxy-6'alpha-(3-hydroxypropyl)-1',2',3',4',5',6'-hexahydrobiphenyl (CP 55940) binds in a specific and saturable manner and the binding sites are heterogeneously distributed in the brain [Devane, Dysarz, Johnson, Melvin and Howlett, Determination and Characterization of a Cannabinoid Receptor in Rat Brain, Molecular Pharm. 34, 605–613 (1988)]. Natural and synthetic cannabinoids and certain of the compounds of the present invention, as more particularly described above, bind to CP 55940 binding sites Classification of whether a molecule is an agonist or an antagonist can be made using a mouse vasa deferentia preparation in vitro, compounds which inhibit contractions in the MVD preparation being considered active as agonists and those which do not inhibit contractions being considered antagonists. It is believed that agonist activity at the cannabinoid receptor mediates the anti-glaucoma actions of cannabinoids, and that agonist activity at this receptor correlates with ocular pressure lowering actions in man. Accordingly the cannabinoid receptor agonist activity of the compounds of the present invention indicate their usefulness in reducing ocular pressure.

The compounds of Formula I of the invention can be prepared for pharmaceutical use by incorporating them in unit dosage form as tablets or capsules for oral or parenteral administration either alone or in combination with suitable adjuvants such as calcium carbonate, starch, lactose, talc, magnesium stearate, gum acacia and the like. Still further, the compounds can be formulated for oral, parenteral or topical administration either in aqueous solutions of the water soluble salts or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus be determined by the clinician after a consideration of all criteria and using his best judgment on the patient's behalf The molecular structures of the compounds of the invention were assigned on the basis of study of their infrared, ultraviolet and NMR spectra. The structures were confirmed by the correspondence between calculated and found values for elementary analyses for the elements.

The following examples will further illustrate the invention without, however, limiting it thereto. All melting points are uncorrected.

PREPARATION OF INTERMEDIATES

The Compounds of Formula II

Preparation 1A

To a solution containing 31.03 g. (0.237 mole) of 2-methylindole and 17.2 g. (0.260 mole) of powdered potassium hydroxide in 100 ml of DMSO at ambient temperature was added, dropwise under nitrogen over a period of one and a half hours, 22.3 ml. (0.26 mole) of epibromohydrin. The reaction mixture was stirred for about eight hours, then poured into water and extracted with diethyl ether. The organic extracts were dried over a drying agent and taken to dryness to give 35.5 g. of 1(2,3-epoxy-1-propyl)-2-methyl-1H-indole as an amber oil.

A solution of the latter in 100 ml. of DMSO was treated with 50 ml. of 40% aqueous methylamine, the solution was stirred for about eight hours, poured into 700 ml. of water and the mixture extracted with diethyl ether. The combined organic extracts were dried over magnesium sulfate, concentrated to about 200 ml, chilled to −20° C., and the solid which separated was collected to give 13.0 g. of 1-(3-methylamino-2-hydroxypropyl)-2-methyl-1H-indole Chromatography on silica gel of the mother liquors from the product, eluting first with 1:1 ethyl acetate:hexane and then with 1:1 ethyl acetate:methanol, gave an additional 20.3 g. of product. Recrystallization of a sample from MDC gave material having m.p. 110°–112° C.

A solution of 10.57 g. (0.048 mole) of the product from above and 6.75 ml. of triethylamine in 150 ml. of MDC was cooled in a dry ice bath and treated dropwise with 5.48 g. (0.048 mole) of chloroacetyl chloride in 40 ml of MDC When addition was complete, the solution was warmed to ambient temperature and the reaction mixture worked up to give 14.15 g. of 1-[3-(N-methyl-N-chloroacetyl)-2-hydroxypropyl]-2-methyl-1H-indole as a light yellow foam.

The latter was dissolved in 50 ml. of THF and the solution added dropwise to a stirred solution of potassium t-butoxide in 100 ml. of THF. The mixture was stirred for about one hour, then quenched with acetic acid, evaporated to dryness in vacuo and the residue partitioned between MDC and water. The organic layer was separated, dried over magnesium sulfate, filtered and taken to dryness to give 10.05 g. of 1-[(4-methyl-5-oxo-2-morpholinyl)methyl]-2-methyl-1H-indole, m.p. 95°–97° C. (from ethyl acetate/hexane). The latter (9.0 g., 0.035 mole) dissolved in 100 ml. of THF was treated with 45 ml. of a 1M solution of borane in THF. The solution was heated to reflux under nitrogen for about twelve hours, then quenched with 100 ml. of methanol and worked up to give 9.1 g. of crude product which was chromatographed on silica gel to give 6.84 g. of 1-[(4-methyl-2-morpholinyl)methyl]-2-methyl-1H-indole as an amber oil. The p-tosylate salt showed m.p. 140°–142° C.

A solution of 50 g. of 1-[(4-methyl-2-morpholinyl)-methyl]-2-methyl-1H-indole in ethyl acetate was treated with 77 g. of (1)-dibenzoyltartaric acid, and the solid which separated was collected and washed with ethyl acetate to give 52.4 g. of the d-base.1-acid salt consisting of (d)-1-[(4-methyl-2-morpholinyl)methyl]-2-methyl-1H-indole (1)-dibenzoyl tartrate, m.p. 149°–150° C., $[\alpha]_D^{25} = -61.4°$.

The free base from the d-base.1-acid salt was liberated by partitioning the salt between ethyl acetate and aqueous sodium bicarbonate and isolation of the free base from the organic layer to give 20.2 g. of (d)-1-[(4-methyl-2-morpholinyl)methyl]-2-methyl-1H-indole, $[\alpha]_D^{25} = +9.5°$.

The free base from the mother liquors from the isolation of the d-base.1-acid salt was liberated as described above, dissolved in ethyl acetate and treated with 38.1 g. of (d)-dibenzoyltartaric acid. The solid which separated was collected, washed with ethyl acetate and dried to give 36 g. of (1)-1-[(4-methyl-2-morpholinyl)-methyl]-2-methyl-1H-indole (d)-dibenzoyltartrate, m.p. 157° C., $[\alpha]_D^{25} = +59.8°$.

Liberation of the free base from the 1-base d-acid salt as before afforded (1)-1-[(4-methyl-2-morpholinyl)-methyl]-2-methyl-1H-indole, $[\alpha]_D^{25} = -10.2°$.

Preparation 1B

Proceeding in a manner similar to that described in Preparation 1A above, 23.4 g. (0.2 mole) of indole and 12.5 g. of powdered potassium hydroxide in 100 ml. of DMSO was reacted with 20.4 g. (0.22 mole) of epichlorohydrin and the product isolated by distillation in vacuo to give 15.3 g. of 1-(2,3-epoxypropyl)-1H-indole, b.p. 150°–160° C./0.15 mm.

The latter, on reaction with 6.56 g. (0.087 mole) of N-methylethanolamine, afforded 21.6 g. of 1-[3-[N-methyl-N-(2-hydroxyethyl)amino]-2-hydroxypropyl]-1H-indole.

A solution of the latter (0.087 mole) and 23.1 g. (0.088 mole) of triphenylphosphine in 300 ml. of MDC was treated in portions with a solution of 15.3 g. (0.088 mole) of diethyl azodicarboxylate in 10 ml of MDC. When the exothermic reaction had subsided, the mixture was stirred for one hour, allowed to stand for about forty-eight hours and then taken to dryness in vacuo. The residue was distilled in vacuo to give 10.0 g. of 1-[(4-methyl-2-morpholinyl)methyl]-1H-indole, b.p. 160°–170° C./0.05 mm.

Preparation 1C

To a solution of 50 g. (0.26 mole) of N-(1-methyl-4-piperidinyl)-N-phenylamine in 1289 ml. of 2N hydrochloric acid at 0° C. was added in a continuous stream while stirring a solution of 21 g. (0.30 mole) of sodium nitrite in 260 ml. of water. The solution was stirred for an additional on hour at 0° C. and then diluted with water and ethyl acetate and neutralized by the careful addition of solid sodium bicarbonate. The organic layer was separated, the aqueous layer was extracted with additional ethyl acetate, and the combined organic extracts were washed with brine, dried over magnesium sulfate and taken to dryness in vacuo to give 53 g. of N-(1-methyl-4-piperidinyl)-N-phenyl-N-nitrosamine as a yellow solid.

The latter (0.24 mole) was dissolved in 1100 ml of THF and the solution treated under nitrogen at 0° C. with a solution of 18 g. of lithium aluminum hydride in 180 ml of THF. When addition was complete the reaction mixture was allowed to warm to room temperature, heated under reflux for one and a half hours and quenched with 36 ml. of brine at 0° C. The mixture was stirred vigorously and treated further with 30 ml. of 3N sodium hydroxide added dropwise followed by 30 ml.

of water at room temperature and then filtered through filter aid. The organic layer was separated, dried over magnesium sulfate and taken to dryness to give an oil, which slowly crystallized, consisting of N-(1-methyl-4-piperidinyl)-N-phenylhydrazine (49.92 g.).

A solution of the latter (0.239 mole) and 32.3 g. (0.195 mole) of phenylthioacetone in 686 ml. of glacial acetic acid was heated under reflux for about twelve hours, treated with an additional 7 g. of phenylthioacetone and 150 ml. of glacial acetic acid and heated an additional two hours. The mixture was concentrated to a small volume, neutralized with solid sodium carbonate and the mixture extracted with ethyl acetate. The organic extracts, on washing with brine, drying over magnesium sulfate and evaporation to dryness, gave an oil which was chromatographed on silica gel, the product being eluted with ethyl acetate. There was thus obtained 53 g. of an oil, a portion of which was dissolved in ethanol and treated with ethanolic hydrogen chloride to produce a white solid which was collected, dried and recrystallized from ethanol to give 6.6 g. of 1-(1-methyl-4-piperidinyl)-2-methyl-3-phenylthio-1H-indole hydrochloride, m.p. 165.5°-169° C.

The latter (46 g., 0.137 mole) dissolved in 450 ml. of absolute ethanol was treated with 10 large spoonfuls of Raney nickel in ethanol, and the mixture was heated under reflux for two hours under nitrogen with stirring. An additional 20 spoonfuls of Raney nickel in ethanol were added, hours and then filtered through filter aid, the filter being washed with ethyl acetate. The combined filtrate was dried over magnesium sulfate and concentrated to a yellow oil which was chromatographed on silica gel, the product being eluted with 5% triethylamine in ethyl acetate. There was thus obtained 18.02 g. of 1-(1-methyl-4-piperidinyl)-2-methyl-1H-indole as a yellow oil Preparation 1D To a suspension of 10.0 g. (0.054 mole) of 3-chloromethyl-1-methylpiperidine in 75 ml. of DMSO was added 6.3 g. (0.113 mole) of potassium hydroxide pellets The mixture was stirred for thirty minutes and then treated dropwise under nitrogen with a solution of 6.1 g. (0.045 mole) of 5-fluoroindole in DMSO while stirring at room temperature. When addition was complete the reaction mixture was stirred at ambient temperature for about twelve hours and then poured into an ice/water mixture. The mixture was extracted with ethyl acetate, and the organic extracts were washed with water, dried over magnesium sulfate, filtered and concentrated to dryness to give 7.6 g. of 1-[(1-methyl-3-piperidinyl)methyl]-5-fluoro-1H-indole as an oil. The hydrochloride 4:1 hydrate has m.p. 190°-191° C.

Preparation 1E

To a suspension of 10.0 g. (0.25 mole) of a 60% sodium hydride dispersion in hexane was added a solution of 31.4 g. (0.20 mole) of ethyl 5-pyrrolidinone-2-carboxylate in 350 ml. of THF. The reaction mixture was stirred at room temperature for one hour, treated with 42.75 g. (0.25 mole) of benzyl bromide, heated under reflux for two hours, taken to dryness in vacuo and the residue partitioned between MDC and water. The organic layer was separated, dried over magnesium sulfate and taken to dryness to give 50.9 g. of an oil which was distilled in vacuo to give 37.0 g. of ethyl 1-benzyl-5-pyrrolidinone-2-carboxylate, b.p. 138°-147° C./0.08-0.12 mm.

The latter was dissolved in 350 ml. of ethanol, the solution treated with 16.6 g. (0.45 mole) of sodium borohydride and the mixture stirred under reflux for three hours and then treated with acetone and water. The liquid was decanted from the reaction mixture and evaporated to dryness in vacuo, and the residue was partitioned between water and MDC. The organic layer was separated, the aqueous layer was washed with additional MDC, and the combined organic extracts were dried over magnesium sulfate and taken to dryness to give 31.6 g. of a colorless oil which solidified and was recrystallized from toluene to give 27.2 g. of 1-benzyl-2-hydroxymethyl-5-pyrrolidinone, m.p. 69°-79° C.

The latter (20.5 g., 0.10 mole) was dissolved in 150 ml. of MDC and the solution treated with 14.3 ml. (0.12 mole) of triethylamine and 0.5 g. of 4-dimethylaminopyridine (DMAP). The mixture was then treated with a solution of 22.8 g. (0.12 mole) of p-toluenesulfonyl chloride in 100 ml. of MDC while stirring in an ice bath, stirred at room temperature for two and a half hours and then concentrated to dryness in vacuo. The residue was taken into ethyl acetate, the solution was filtered, the filtrate washed with sodium bicarbonate, dried over magnesium sulfate and evaporated to dryness to give a pale yellow oil which slowly solidified to give 1-benzyl-2-hydroxymethyl-5-pyrrolidinone p-toluenesulfonate, m.p. 72°-78° C.

A solution of 15.7 g. (0.12 mole) of 2-methylindole in 50 ml. of DMSO was treated with 17 g. of powdered potassium hydroxide and then with a solution of 23.3 g. (0.065 mole) of the pyrrolidinone p-toluenesulfonate described above dissolved in 20 ml. of DMSO. When the resulting exothermic reaction had subsided, the mixture was stirred for two hours at ambient temperature and then poured into water and the mixture extracted with MDC. The combined organic extracts were washed with water, dried over magnesium sulfate, and taken to dryness to afford 30 g. of a pale amber oil which gradually crystallized and was collected to give 17.3 g. of 1-[(1-benzyl-5-oxo-2-pyrrolidinyl)methyl]-2-methyl-1H-indole, m.p. 130°-131.5° C.

The latter (31.8 g., 0.10 mole) in 100 ml of THF was added slowly with stirring at room temperature to 300 ml. of a 1.2 M solution of methyl lithium in diethyl ether. The mixture was stirred at ambient temperature for thirty minutes and then added with stirring to 125 ml. of a 1.0 M solution of lithium aluminum hydride in THF at room temperature. The mixture was stirred at ambient temperature for two and a half hours and then decomposed by the addition of 100 ml. of 5N sodium hydroxide followed by 100 ml. of water. The reaction mixture was then taken to dryness in vacuo and the residue partitioned between MDC and water and filtered through filter aid. The organic layer was separated from the filtrate, dried over magnesium sulfate and taken to dryness in vacuo to give 29 g. of a clear amber oil which was chromatographed on silica gel, eluting with hexane:MDC to give 5.2 g. of 1-[(1-benzyl-5-methyl-2-pyrrolidinyl)methyl]-2-methyl-1H-indole as a straw colored oil.

Preparation 1F

Following a procedure similar to that described in Preparation 1D above, a solution of 95 g. (0.735 mole) of 3-hydroxymethyl-1-methylpiperidine in 600 ml. of MDC was cooled to 0° C. and treated dropwise with 53.6 ml. of thionyl chloride. When addition was complete, the reaction mixture was heated to reflux for one hour and then taken to dryness to give 135 g. of 3-chloromethyl-1-methylpiperidine.

To a suspension of 3.9 g. of a 60% dispersion of sodium hydride in hexane in 200 ml. of DMF was added a solution of 9.5 g. (0.081 mole) of indole in 200 ml. of DMF with stirring at room temperature. The mixture was then treated with a mixture of 18 g. (0.098 mole) of 3-chloromethyl-1-methylpiperidine hydrochloride and a catalytic amount of sodium iodide, heated on a steam bath for about twelve hours and then poured into one liter of water and extracted with ethyl acetate. The combined organic extracts were extracted with 2N hydrochloric acid, the aqueous extracts were basified by the addition of solid sodium carbonate and extracted with ethyl acetate. The organic extracts, on drying over magnesium sulfate and evaporation to dryness, afforded 12 g. of 1-[(1-methyl-3-piperidinyl)methyl]-1H-indole as a yellow brown oil.

Preparation 1G

Following a procedure similar to that described in Preparation 1D above, a solution of 74.3 g. (0.57 mole) of 2-methylindole in 600 ml. of DMF was added to a stirred suspension of 27.4 g. of a 60% sodium hydride in hexane dispersion in 1500 ml of DMF The reaction mixture was stirred for thirty minutes and then treated with a solution of 100 g. (0.68 mole) of 3-chloromethyl-1-methylpiperidine in 1 liter of DMF. The product was isolated in the form of the free base as described in Preparation 1F to give 104 g. of 1-(1-methyl-3-piperidinyl)methyl]-2-methyl-1H-indole as a reddish brown oil.

Preparation 1H

Proceeding in a manner similar to that described in Preparation 1D above, in two separate runs, 11.7 g. (0.1 mole) of indole were reacted with 15.5 g. (0.11 mole) of 1-methyl-2-chloromethylpiperidine in 50 ml. of DMSO in the presence of 6 g. (0.29 mole) of powdered potassium hydroxide, to give a total of 43.5 g. of crude product which was distilled in vacuo at 115°–120° C./0.3 mm to give 38.5 g. of 1-[(1-methyl-2piperidinyl)methyl]-1H-indole as a pale yellow oil.

Preparation 1I

Following a procedure similar to that described in Preparation 1D above, 48 g. (0.17 mole) of 5-fluoro-2-isopropylindole was reacted with 20 g. (0.11 mole) of 1-methyl-3-hydroxymethylpiperidine p-toluenesulfonate in the presence of 39.9 g. (0.62 mole) of potassium hydroxide pellets in DMSO to give 3.0 g. of 1-[(1-methyl-2-piperidinyl)methyl]-5-fluoro-2-isopropyl-1H-indole hydrochloride 1/4 H$_2$O, m.p. 190°–191° C.

Preparation 1J

Following a procedure similar to that described in Preparation 1D above, 16.9 g. (0.106 mole) of 2-isopropylindole was reacted with 51 g. (0.18 mole) of 1-methyl-3-hydroxymethylpiperidine p-toluenesulfonate in DMSO in the presence of 37.4 g. (0.58 mole) of potassium hydroxide pellets to give 1-[(1-methyl-3-piperidinyl)methyl]-2-isopropyl-1H-indole hydrochloride, m.p. 144°–148° C.

Preparation 1K

Following a procedure similar to that described in Preparation 1D above, 6.56 g. (0.05 mole) of 2-methylindole was reacted with 8.3 g. (0.049 mole) of 1-methyl-2-chloromethylpyrrolidine in 50 ml. of DMSO in the presence of 10 g. (0.18 mole) of powdered potassium hydroxide to give 3.92 g. of 1-[(1-methyl-2-pyrrolidinyl)methyl]-2-methyl-1H-indole, b.p. 120.5° C./0.05 mm.

Preparation 1L

Following a procedure similar to that described in Preparation 1D above 11.27 g. (0.086 mole) of 2-methylindole was reacted with 28.44 g. (0.086 mole) of 1-benzyl-3-hydroxypyrrolidine p-toluenesulfonate in 110 ml. of DMSO in the presence of 6.75 g. (0.12 mole) of powdered potassium hydroxide to give 10.19 g. of 1-(1-benzyl-3-pyrrolidinyl)-2-methyl-1H-indole as a viscous orange oil.

Preparation 1M

Following a procedure similar to that described in Preparation 1D above, 29.1 g. (0.222 mole) of 2-methylindole was reacted with 38.8 g. (0.137 mole) of 1-methyl-2-hydroxymethyl-5-pyrrolidone p-toluenesulfonate in DMSO in the presence of 35 g. (0.63 mole) of powdered potassium hydroxide to give two crops, totaling 24.5 g., of 1-[(1-methyl-5-oxo-2pyrrolidinyl)methyl]-2-methyl-1H-indole, m.p. 102°–104° C.

Following a procedure similar to that described in Preparation 1E above, the latter was reacted with 300 ml. of a 1.2 M solution of methyl lithium in ether, and the resulting product was reduced with 125 ml. of a 1.0 M solution of lithium aluminum hydride in THF There was thus obtained a mixture of the cis and trans isomers of 1-[(1,5-dimethyl-2pyrrolidinyl)methyl]-2-methyl-1H-indole which, on chromatography on silica gel, eluting with 5% ether/MDC, afforded 2.75 g. of the cis isomer.

Preparation 1N

To a suspension of 8.7 g. (0.22 mole) of a 60% sodium hydride in hexane dispersion in 100 ml. of DMF was added 21.3 g. (0.18 mole) of indole, and the mixture was stirred for one hour at ambient temperature, cooled to 0° C., diluted with 500 ml. of DMF and then treated with vigorous stirring with 33.1 g. (0.22 mole) of α-chloro-N-methyl-N-methoxyacetamide in 75 ml. of DMF. When addition was complete the reaction mixture was quenched with 200 ml. of water and extracted with ethyl acetate. The combined organic extracts were washed with brine, dried and taken to dryness to give 29.4 g. of α-(1-indolyl)-N-methyl-N-methoxyacetamide as a slightly purple oil.

The latter (13.6 g., 0.059 mole) in diethyl ether was treated, with cooling and under nitrogen, with a solution of 0.176 mole of tetramethyl ethylene disilylaminopropyl magnesium bromide in diethyl ether. When addition was complete, the reaction mixture was stirred for one hour at ambient temperature, treated with 450 ml. of a 10% hydrogen chloride in ethanol solution and then stirred for one and a half hours. The mixture was then treated with 7.5 g. of sodium borohydride at 0° C., stirred at ambient temperature for about twelve hours and then taken to dryness. The residue was partitioned between diethyl ether and water, the aqueous layer was separated and basified with 5N sodium hydroxide, extracted with diethyl ether, and the combined organic extracts were dried and taken to dryness to give 13.5 g. of an oil which was chromatographed on silica gel, eluting with 2% triethylamine in ethyl acetate, to give 6.75 g. of 1-[1-(4,5-dihydro-2-pyrrolyl)-1-ethyl]-1H-indole and 2.4 g. of 1-[1-(2-pyrrolyl)-1-ethyl]-1H-indole.

The sample of 1-[1-(4,5-dihydro-2-pyrrolyl)-1ethyl]-1H-indole (0.0318 mole) wa dissolved in 200 ml. of ethanol and treated at 0° C. with 1.3 g. of sodium borohydride. The reaction mixture was stirred for about twelve hours, then taken to dryness in vacuo and the residue partitioned between water and ethyl acetate. The combined organic extracts were taken to dryness to give an oil which was chromatographed on silica gel, eluting with 2% triethylamine in ethyl acetate, to give 3.2 g. of the anti form of 1-[1-(2-pyrrolidinyl)-1ethyl]-1H-indole and 1.0 g. of the syn-form thereof.

Preparation 1-O

Following a procedure similar to that described in Preparation 1D above, 29.7 g. (0.227 mole) of 2-methylindole was reacted with 64.1 g. (0.227 mole) of 1-methyl-5-(p-tosyloxy)methyl)-2-pyrrolidinone in 250 ml. of DMSO in the presence of 23.0 g. (0.48 mole) of potassium hydroxide flakes to give 15.0 g. of 2-methyl-1-[(1-methyl-5-oxo-2-pyrrolidinyl)-methyl]-1H-indole, m.p. 104°-105° C.

Preparation 1P

Following a procedure similar to that described in Preparation 1D above, 74.3 g. (0.57 mole) of 2-methylindole was reacted with 100 g. (0.68 mole) of 1-methyl-3-chloromethylpiperidine in the presence of 27.4 g. of a 60% sodium hydride in hexane dispersion and 5 g. of sodium iodide in 1500 ml. of DMF. About one fifth of the crude product thus obtained was converted to the hydrochloride salt to give 3 g. of 2-methyl-1-[(1-methyl-3-piperidinyl)methyl]-1H-indole hydrochloride, m.p. 177°-179° C. (crystallized from methanol/diethyl ether).

Preparation 1Q

Following a procedure similar to that described in Preparation 1D above, 20 g. (0.15 mole) of 2-methylindole was reacted with 29 g. (0.18 mole) of 1-methyl-2-(2-chloroethyl)-piperidine hydrochloride in DMF in the presence of 7.2 g. of a 60% sodium hydride in hexane dispersion. There was thus obtained 10 g. of 2-methyl-1-[2-(1-methyl-2-piperidinyl)-ethyl]-1H-indole, m.p. 61°-62° C. (from ethanol).

Preparation 1R

To 350 ml. of a solution containing 0.49 mole of methyl lithium in diethyl ether was added a solution of 45.9 g. (0.144 mole) of 2-methyl-1-[(1-benzyl-5-oxo-2-pyrrolidinyl)methyl]-1H-indole in 150 ml. of THF while stirring and cooling in an ice bath. Work up of the reaction mixture using the procedure described above in Preparation 1E afforded 2.1 g. of trans 2-methyl-1-[(1-benzyl-5-methyl-2-pyrrolidinyl)methyl-1H-indole hydrochloride, m.p. 225°-228° C. (from isopropanol/ethanol) and 800 mg. of cis 2-methyl-1-[(1-benzyl-5-methyl-2-pyrrolidinyl)methyl]-1H-indole, m.p. 75°-77° C. (from cyclohexane).

The Compounds of Formula VI

Preparation 2A

To a solution of 46 ml. of 2.9M methyl magnesium bromide in diethyl ether was added a solution of 17.5 g. (0.12 mole) of 2-ethylindole in 70 ml. of diethyl ether while stirring under nitrogen and cooling in an ice bath. When addition was complete, the ice bath was removed, and the reaction mixture was stirred for forty-five minutes at ambient temperature, then cooled again in an ice bath and treated, over a fifteen minute period, with a solution of 22 g. (0.13 mole) of 4-methoxybenzoyl chloride in 25 ml. of diethyl ether. The mixture was then heated under reflux on a steam bath for two hours, treated with 200 ml. of a saturated solution of ammonium chloride and the ether distilled off on a steam bath with stirring. The residue was mixed with water, and the solid which separated was collected, washed first with water, and then with diethyl ether and dried in vacuo to give 38 g. of a white solid which was recrystallized from ethyl acetate to give 27.7 g. of 2-ethyl-3-(4-methoxybenzoyl)indole, m.p. 204.5°-206.5° C.

Preparation 2B

Following a procedure similar to that described in Preparation 2A above, 42 g. (0.036 mole) of indole was reacted with 150 ml. of a 2.9M solution of methyl magnesium bromide in diethyl ether, and the resulting Grignard reagent was treated with 47.5 ml. (63.7 g., 0.039 mole) of 2-fluorobenzoyl chloride in diethyl ether. There was thus obtained 3-(2-fluorobenzoyl)indole as an oil.

Preparation 2C

Following a procedure similar to that described in Preparation 2A above, 30.7 g. (0.262 mole) of indole was reacted with 112.5 ml. of a 2.8 M solution of methyl magnesium bromide in MDC, and the resulting Grignard reagent was treated with a solution of 50 g. (0.26 mole) of 1-naphthoyl chloride in 50 ml. of MDC. There was thus obtained 57.3 g. of 3-(1-naphthylcarbonyl)indole as an oil.

Preparation 3A

Preparation 3A

To a suspension of 2.0 g. (0.053 mole) of lithium aluminum hydride in 200 ml. of THF was added a solution of 7 g. (0.044 mole) of methyl 1-methyl-1,2,3,6-tetrahydro-3-pyridine carboxylate over a thirty minute period, and the mixture was then stirred at −50° C. for three hours. The unreacted lithium aluminum hydride was destroyed by the careful addition of water followed by 40 ml. of 10% sodium hydroxide followed by an additional 40 ml. of water. The reaction mixture was filtered, and the organic phase was separated from the aqueous phase, washed with brine, dried over magnesium sulfate and taken to dryness to give 4.2 g. of 3-hydroxymethyl-1-methyl-1,2,3,6-tetrahydropyridine as a yellow oil.

A solution of the latter (2.0 g., 0.016 mole) in 50 ml. of methylene dichloride was cooled to 0° C., treated with 2.25 g. (0.019 mole) of thionyl chloride, and the reaction mixture was heated under reflux for one hour and then taken to dryness. The residue was twice mixed with 50 ml. of toluene and taken to dryness to remove excess thionyl chloride thus affording 2.9 g. of 3-chloromethyl-1-methyl-1,2,3,6-tetrahydropyridine hydrochloride as a white solid.

Preparation 3B

Following a procedure similar to that described in Preparation 3A above, 90 g. (0.49 mole) of ethyl 1-ethyl-3-piperidine carboxylate dissolved in 200 ml. of THF was reduced with 20 g. of lithium aluminum hydride in 1500 ml. of THF to give 64 g. of 1-ethyl-3-hydroxymethylpiperidine as a light yellow oil, which was dissolved in 500 ml. of MDC and reacted with 35 ml. (0.48 mole) of thionyl chloride. There was thus obtained 84 g. of 3-chloromethyl-1-ethylpiperidine hydrochloride.

Preparation 3C

Following a procedure similar to that described in Preparation 3A above, 23.75 g. (0.08 mole) of ethyl 1-benzhydryl-2-azetidinyl carboxylate in 240 ml. of diethyl ether was reduced with 6.1 g. (0.16 mole) of lithium aluminum hydride in 600 ml. of diethyl ether to give 25.2 g. of 1-benzhydryl-2-hydroxymethylazetidine, 24.7 g. (0.098 mole) of which was dissolved in 265 ml. of MDC and treated with 15.8 ml. (0.11 mole) of triethylamine and 0.5 g. of DMAP followed by 21.5 g. (0.113 mole) of p-toluenesulfonyl chloride to give 39.6 g. of 1-benzhydryl-2-hydroxymethylazetidine p-toluene-sulfonate as an oil.

Preparation 3D

Following a procedure similar to that described in Preparation 3A above, 22 g. (0.15 mole) of 1,4-dimethyl-2-hydroxymethylpiperazine (Preparation 5E) was reacted with 23.7 ml. (0.321 mole) of thionyl chloride in 500 ml. of MDC to give 11.21 g. of 2-chloromethyl-1,4-dimethylpiperazine as an oil.

The Compounds of Formula VII

Preparation 4A

To a solution of 13.2 g. (0.0498 mole) of 3-(4-methoxybenzoyl)-2-methylindole in 250 ml. of MDC was added 100 ml. of 50% sodium hydroxide and 170 mg of tetrabutyl ammonium sulfate. The solution was cooled to 20° C. and then treated dropwise with a solution of 14 ml. of methanesulfonyl chloride in 15 ml. of MDC while maintaining the temperature at between 25° and 29° C. When addition was complete the reaction mixture was poured into water, the organic layer was separated and the aqueous layer extracted with additional MDC. The combined organic extracts were washed with water, dried over magnesium sulfate and taken to dryness in vacuo to give a tan solid which was triturated with acetonitrile, filtered and dried to give 13.4 g. of 1-methylsulfonyl-2-methyl-3-(4-methoxybenzoyl)-1H-indole.

Preparation 4B

Following a procedure similar to that described in Preparation 4A above, about 5 g. of 3-(1-naphthylcarbonyl)indole was reacted with 5.7 ml. of methanesulfonyl chloride in the presence of 0.5 g. of tetrabutylammonium hydrogen sulfate in 140 ml. of MDC and 50 ml. of 50% aqueous sodium hydroxide. The crude product was triturated with acetonitrile, filtered and dried to give 4.4 g. of 1-sulfonylmethyl-3-(1-naphthylcarbonyl)-1H-indole.

The Compounds of Formula VIII

Preparation 5A

To a suspension of 0.9 g. (1.02 mole) of lithium aluminum hydride in 50 ml. of THF at 0° C. under a nitrogen atmosphere was added a solution of 2.0 ml. (0.02 mole) of 1-methylpyrrol-2-carboxaldehyde. When the strongly exothermic reaction had subsided, the reaction mixture was cooled to 0° C. and quenched by the careful addition of 10 ml. of water. The reaction mixture was dried over magnesium sulfate, filtered and taken to dryness in vacuo to give 2.0 g. of 2-hydroxymethyl-1-methylpyrrole.

Preparation 5B

To a suspension of 15.7 g. (0.413 mole) of lithium aluminum hydride in 1 liter of THF was added at room temperature under a nitrogen atmosphere a solution of 26.0 g. (0.138 mole) of ethyl 4-methyl-3-thiomorpholinecarboxylate [Khim. Getero. Soedin., 10, 1357-8 (1983)] in THF. The reaction mixture was worked up as described in Preparation 5A above to give 18.55 g. of 3-hydroxymethyl-4-methylthiomorpholine as a clear, viscous colorless oil, b.p. 75°-100° C./0.15 mm.

Preparation 5C

Following a procedure similar to that described in Preparation 5A above, 10.0 g. (0.081 mole) of 2-acetyl-1-methylpyrrole in THF was reduced with 3.8 g. (0.10 mole) of lithium aluminum hydride to give 10.0 g. of 2-(1-hydroxyethyl)-1-methylpyrrole as a clear colorless oil.

Preparation 5D

To a vigorously stirred solution of 10 g. (0.095 mole) of d,l-serine in aqueous sodium hydroxide (prepared by dissolving 3.8 g. of solid in 50 ml. of water) at room temperature was added 20 ml. of benzaldehyde, and the mixture was stirred for thirty minutes and then cooled to 5° C. The resulting solution was treated with 2 g. of sodium borohydride added in portions over a twenty-five minute period while maintaining the temperature below about 10° C. The mixture was stirred for one hour at room temperature, then washed with diethyl ether and the aqueous solution adjusted to pH 6.5 by the addition of dilute hydrochloric acid. The solid which separated was collected by filtration and dried to give 7.13 g. of α-benzylamino-β-hydroxypropionic acid.

A solution of the latter (0.037 mole) in dilute sodium hydroxide was cooled to 0° C. and the solution treated dropwise with a total of 30 ml. of chloroacetyl chloride while maintaining the pH at 14. When addition was complete the reaction mixture was stirred for two hours at 25° C., washed with chloroform and the raffinate acidified to pH 1 by the addition of 6N hydrochloric acid. Extraction of the aqueous mixture with chloroform and evaporation of the combined extracts to dryness afforded 5.4 g. of 4-benzyl-5-oxo-3-morpholinecarboxylic acid.

The latter (0.02 mole) suspended in toluene was reduced with 32 ml. of a 3.4M solution of sodium bis(methoxyethoxy) aluminum hydride in toluene while maintaining the temperature at 0° C., and the reaction mixture was worked up as described in Preparation 5A above. There was thus obtained 3.49 g. of 4-benzyl-3-hydroxymethylmorpholine as a yellow oil.

Preparation 5E

A mixture of 36 g. (0.23 mole) of N,N'-dimethylethylenediamine, 33 ml. (0.23 mole) of ethyl α,β-dibromopropionate, 48 g. (0.45 mole) of sodium carbonate and 64 ml. (0.45 mole) of triethylamine in 300 ml. of methanol was heated under reflux for five and a half hours, and then cooled, filtered and the precipitate washed with methanol. The combined filtrates were taken to dryness in vacuo, and the residue was partitioned between water and diethyl ether. The aqueous layer was extracted with additional diethyl ether, and the combined ether extracts were dried and taken to dryness to give 46.4 g. of crude product as an oil which was distilled in vacuo to give 33.47 g. of ethyl N,N'-dimethylpiperazine-2-carboxylate, b.p. 110°–145° C./24 mm.

The latter (0.18 mole) was reduced with 26.5 g. (0.70 mole) of lithium aluminum hydride in 300 ml. of diethyl ether using the procedure described in Preparation 3A above to give 23.16 g. of 1,4-dimethyl-2-hydroxymethylpiperazine, b.p. 110°–140° C./23 mm.

The Compounds of Formula IX

Preparation 6

A solution of 15 g. (0.057 mole) of 2-methyl-3-(4-methoxybenzoyl)indole in 120 ml. of DMF under nitrogen was treated with 1.36 g. (0.057 mole) of sodium hydride at 0° C. The mixture was allowed to warm to room temperature over a period of two hours and then treated with 20 ml. of chloromethyl trimethylsilane and a catalytic amount of sodium iodide and stirred at room temperature for about twelve hours. The solvent was removed by distillation in vacuo, the residue was mixed with 500 ml. of diethyl ether and the mixture filtered.

The filtrate was taken to dryness, and the residue was chromatographed on silica gel, eluting with 30% ethyl acetate/hexane. The product, consisting of 16.5 g. of 2-methyl-3-(4-methoxybenzoyl)-1-trimethylsilylmethyl-1H-indole, was isolated as a light amber oil from the initial, more mobile fractions.

Miscellaneous Processes for Preparation of Intermediates

Preparation 7A

To a solution of 10.0 g. (0.08 mole) of 1-methyl-2-(1-hydroxyethyl)pyrrole in toluene was added 21.0 g. (0.062 mole) of 2-methyl-3-(4-methoxybenzoyl)-1-methylsulfonyl-1H-indole in toluene, and the reaction mixture was treated with 1.63 g. (0.066 mole) of 97% sodium hydride. The mixture was stirred for ten minutes at room temperature until the reaction had subsided, heated in an oil bath at 110° C. for about an hour and a half and then cooled, quenched with ice and extracted with ethyl acetate. The combined organic extracts on work up afforded 7 g. of 2-methyl-3-(4-methoxybenzoyl)-1-[1-(1-methyl-2-pyrrolyl)ethyl]-1H-indole, m.p. 153°–154° C. (from ethyl acetate).

Following a procedure similar to that described in Preparation 7A above, the following compounds of Formula I in Table A were prepared by reaction of an appropriate 2-$R_2$-$R_4$-substituted-3-arylcarbonyl-1-methylsulfonyl-1H-indole with an appropriate C-hydroxy-lower-alkyl-N-aromatic heterocycle in the presence of sodium hydride. In Table A and in the other tables which follow, various heterocyclic and other groups are abbreviated as follows:

| | |
|---|---|
| pip. | piperidinyl |
| mor. | morpholinyl |
| azep. | hexahydroazepinyl |
| pyr. | pyrrolyl |
| pyrd. | pyrrolidinyl |
| pzl. | piperazinyl |
| pyd. | pyridinyl |
| pyz. | pyrazinyl |
| 4H-pyd. | 1,2,5,6-tetrahydropyridinyl |
| azet. | azetidinyl |
| thiaz. | 2,3,4,5,6,7-hexahydro-1,4-thiazepinyl |
| thiom. | thiomorpholinyl |
| ind. | indolinyl |
| bzl. | benzyl |
| bzhyd. | benzhydryl |

TABLE A

| Prepn. | $R_3$ | $R_2R_4$ | (Alk)$_n$/Het | Base/Salt | m.p./solv. |
|---|---|---|---|---|---|
| 7B | 4-CH$_3$OC$_6$H$_4$ | CH$_3$/H | CH$_2$<br>1-CH$_3$-2-pyr. | base | 152–153 |
| 7C | 4-CH$_3$OC$_6$H$_4$ | CH$_3$/H | CH$_2$<br>1,5-(CH$_3$)$_2$-2-pyr. | base | 158–159<br>EtOAc |
| 7D | 1-naphthyl | CH$_3$/H | CHCH$_3$<br>1-CH$_3$-2-pyr. | base | 172–174 |

Preparation 8A

A solution of 10 g. (0.04 mole) of 3-(4-methoxybenzoyl)indole in 125 ml. of DMF was treated with stirring with 1.92 g. (0.08 mole) of 97% sodium hydride, the mixture was stirred for one hour, then treated with a solution of 15.5 g. (0.04 mole) of 1-(4-methoxybenzyl)-5-toluenesulfonyloxymethyl-2-pyrrolidinone in 125 ml. of DMF followed by 1 g. of potassium iodide, and stirred on a steam bath for approximately eighteen hours, then quenched with ice and water and taken to dryness in vacuo. The residue was partitioned between ethyl acetate and water, and the organic layer was separated, washed with brine, dried over magnesium sulfate and taken to dryness to give 19.7 g. of crude product which was recrystallized from ethyl acetate to give 9.8 g. of 3-(4-methoxybenzoyl)-1-{[1-(4-methoxybenzyl)-5-oxo-2-pyrrolidinyl]-methyl}-1H-indole, m.p. 159°–160° C.

Following a procedure similar to that described in Preparation 8A above, the following compounds of Formula I in Table B, where N=B is an aromatic N-heterocycle and $R_4$ is hydrogen, were prepared by reaction of an appropriate 2-$R_2$-3-arylcarbonylindole with an appropriate N-aromatic heterylmethyl chloride in the presence of a strong base.

TABLE B

| Prepn. | $R_2$ | $R_3$ | (Alk)/Het | Base/Salt | m.p./solv. |
|---|---|---|---|---|---|
| 8B | CH$_3$ | 4-CH$_3$OC$_6$H$_4$ | 2-pyd. | base | 140–142<br>EtOAc |
| 8C | CH$_3$ | 4-CH$_3$OC$_6$H$_4$ | 4-pyd. | base | 170–172<br>EtOAc/Et$_2$O |
| 8D | CH$_3$ | 4-CH$_3$OC$_6$H$_4$ | 2-pyz. | base | 143–144<br>i-PrOH |
| 8E | CH$_3$ | 4-CH$_3$OC$_6$H$_4$ | 3-pyd. | base | 123.5–125.5<br>CH$_3$CN |
| 8F | CH$_3$ | 4-CH$_3$OC$_6$H$_4$ | 3-pyd. | Me p-tosylate (a) | 177–178<br>i-PrOH |

TABLE B-continued

| Prepn. | R$_2$ | R$_3$ | (Alk)/Het | Base/Salt | m.p./solv. |
|---|---|---|---|---|---|
| 8G | H | 1-naphthyl | 2-pyd. | base | — |

(a) Prepared by reaction of the product with methyl p-toluenesulfonate in acetone.

Preparation 9A

To a stirred mixture of 58 g. (0.93 mole) of aluminum chloride in 240 ml. of MDC was added a solution of 28.6 g. (0.18 mole) of 2-fluorobenzoyl chloride in 100 ml. of MDC. The resulting mixture was stirred for two hours and then added dropwise to a solution of 29 g. (0.149 mole) of 1-(3-pyridinyl)-1H-indole in 200 ml. of MDC. When addition was complete the reaction mixture was stirred for fifteen minutes and then poured into 1 liter of water. The organic layer was separated, washed with aqueous sodium bicarbonate, dried over magnesium sulfate and taken to dryness in vacuo to give 50 g. of a red oil. The latter was dissolved in 200 ml. of isopropanol, the solution was treated with 10 ml. of concentrated hydrochloric acid, and the solid which separated was collected and dried to give 24.8 g. of product which was recrystallized from ethanol to give 3-(2-fluorobenzoyl)-1-(3-pyridinyl)-1H-indole hydrochloride, m.p. 205°–212° C.

Following a procedure similar to that described in Preparation 9A above, the following compounds of Formula I in Table C, where N=B is an aromatic N-heterocycle, were prepared by reaction of an appropriate 2-R$_2$-R$_4$-substituted-1-[(C-attached-N-aromatic heteryl)(Alk)$_n$]-1H-indole with an appropriate aryl carboxylic acid chloride in the presence of aluminum chloride.

an ice bath and treated dropwise with stirring with a solution of 7.6 g. (0.11 mole) of sodium nitrite in 20 ml. of water. When addition was complete the mixture was treated with ethyl acetate and solid sodium bicarbonate, the organic layer was separated and the aqueous layer washed with additional ethyl acetate. The combined organic extracts were dried over magnesium sulfate and taken to dryness in vacuo to give 22.6 g. of 3-[1-(phenyl-N-nitrosoamino)ethyl]pyridine as an orange gray oil.

The latter was dissolved in a solution of 30 ml. of water and 30 ml. of glacial acetic acid and the solution treated with stirring with 20 g. (0.31 mole) of zinc dust added in portions over a period of about an hour and a half. The reaction mixture was then filtered, the filtrate taken to dryness in vacuo, and the residue partitioned between chloroform and water and treated with excess solic sodium bicarbonate. The organic layer was separated, the aqueous layer was washed with additional chloroform, and the combined organic extracts were dried over magnesium sulfate and taken to dryness in vacuo to give 19 g. of N-[1-(3-pyridinyl)ethyl]-N-phenylhydrazine as a pale yellow oil.

A solution of 17 g. (0.09 mole) of the latter, 19.2 g. (0.10 mole) of 4-(4-methoxyphenyl)-2,4-butanedione and 0.5 g. of toluenesulfonic acid in 200 ml. of toluene was heated under reflux with stirring for two and a half hours and then taken to dryness in vacuo. The residue was dissolved in 200 ml. of glacial acetic acid and

TABLE C

| Prepn. | R$_3$ | R$_2$/R$_4$ | (Alk)$_n$/Het | Base/Salt | m.p./solv. |
|---|---|---|---|---|---|
| 9B | 4-CH$_3$OC$_6$H$_4$ | CH$_3$/H | —<br>3-pyd. | HCl.¼ H$_2$O | 194–200<br>i-PrOH |
| 9C | 4-CH$_3$OC$_6$H$_4$ | CH$_3$/H | —<br>3-pyd. | Me p-tosylate | 155–158<br>i-PrOH |
| 9D | 4-CH$_3$OC$_6$H$_4$ | H/H | —<br>3-pyd. | base | 129–131<br>toluene |
| 9E | 2-FC$_6$H$_4$ | H/H | CHCH$_3$<br>3-pyd. | base | 133–135<br>CH$_3$CN |

Preparation 10

A solution of 50 ml. (0.46 mole) of 3-acetyl pyridine, 42 ml. (0.46 mole) of aniline, 10 ml. of glacial acetic acid and 1 liter of toluene was stirred and heated under reflux under a Dean-Stark water trap for seventy-two hours and the reaction mixture taken to dryness to give 3-[(1-phenylimino)ethyl]pyridine as a yellow oil.

The latter was dissolved in 1 liter of ethanol, and the solution treated with 20.2 g. (0.53 mole) of sodium borohydride added in two equal portions approximately one hour apart. The mixture was then heated under reflux for one hour, stirred at room temperature for thirty minutes, treated with a little water and taken to dryness in vacuo. The residue was partitioned between ethyl acetate and water, the organic layer was separated, and the aqueous layer washed with additional ethyl acetate. The combined organic extracts were dried over magnesium sulfate and taken to dryness to give 44 g. of a solid which was recrystallized from cyclohexane to give 41.1 g. of 3-[1-(phenylamino)ethyl]pyridine, m.p. 131°–132.5° C.

The latter (19.8 g., 0.1 mole) was dissolved in 100 ml. of 2N hydrochloric acid, and the solution was cooled in heated under reflux for ninety-two hours. Evaporation of the reaction mixture to dryness in vacuo afforded an orange brown residue which was dissolved in MCD and chromatographed in 760 g. of silica gel, the product being eluted with 1:1 diethyl ether:MDC. The crude product thus obtained was dissolved in isopropanol, the solution treated with concentrated hydrogen chloride, then with a little diethyl ether, and the solid which separated was collected and recrystallized from isopropanol/diethyl ether to give 5.07 g. of 2-methyl-3-(4-methoxybenzoyl)-1-[1-(3-pyridinyl)ethyl]-1H-indole hydrochloride, m.p. 180°–183° C.

Preparation 11

To 200 ml. of diethyl ether containing 33 ml. of 3M methyl magnesium bromide was added a solution of 13.1 g. (0.1 mole) of 2-methylindole in a small amount of diethyl ether. The mixture was stirred for one hour, and then treated with 21.8 g. (0.01 mole) of diphenyl disulfide dissolved in about 25 ml. of THF. The reaction mixture was stirred at room temperature for about twelve hours, taken to dryness, the solvent replaced with THF, and the solution heated under reflux for four hours and then allowed to stand at room temperature for about twelve hours. The mixture was treated with water and extractively worked up with diethyl ether and 10% sodium hydroxide. The combined organic extracts were evaporated to dryness and chromatographed o silica gel in 1:1 diethyl ether:hexane to give 10.7 g. of 2-methyl-3-phenylthioindole.

The latter (4.7 g., 0.197 mole) was alkylated with 8.0 g. (0.03 mole) of 1-methyl-3-(p-toluenesulfonyloxy)-piperidine in 220 ml. of DMF in the presence of 1.6 g. (0.04 mole) of sodium hydride using the procedure described above in Preparation 8A. The product, resulting from ring contraction of the alkylating agent, was isolated in the form of the hydrochloride salt to give 2.3 g. of 2-methyl-3-phenylthio-1-[(1-methyl-2-pyrrolidinyl)methyl]-1H-indole hydrochloride, m.p. 163°–165° C.

PREPARATION OF THE FINAL PRODUCTS

By Acylation of the Compounds of Formula II

Example 1A

To a stirred slurry of 5.86 g. (0.44 mole) of aluminum chloride in MDC at room temperature under a nitrogen atmosphere was added a solution of 5.0 g. (0.29 mole) of 4-methoxybenzoyl chloride in 30 ml of MDC. The resulting solution was stirred for one hour and then added in a slow stream to a solution of 5.96 g. (0.024 mole) of 1-[(4-methyl-2morpholinyl)methyl]-2-methyl-1H-indole in 75 ml of MDC. The reaction mixture was stirred for thirty minutes and then poured into 250 g. of ice/water and neutralized with saturated sodium bicarbonate solution. The organic layer was separated, dried over magnesium sulfate, filtered and taken to dryness to give 8.3 g. of an amber oil which was dissolved in dry diethyl ether and treated with an ethereal solution of hydrogen chloride. The solid which separated was collected, dried and recrystallized from ethanol and ethereal hydrogen chloride to give 6.68 g. of 1-[(4-methyl-2-morpholinyl)methyl]-2-methyl-3-(4-methoxybenzoyl)-1H-indole hydrochloride, m.p. 169°–171° C.

The free base liberated from the hydrochloride salt gives m.p. 169°–170° C. (from ethyl acetate).

Reaction of 14.0 g. (0.057 mole) of (1)-1-[(4-methyl-2-morpholinyl)methyl]-2-methyl-1H-indole (Preparation 1A) with 18.9 ml. (0.115 mole) of 4-methoxybenzoyl chloride in MDC in the presence of 19 g. (0.14 mole) of aluminum chloride and isolation of the product in the form of the hydrochloride salt afforded 10.0 g. of (1)-1-(4-methyl-2-morpholinyl)-methyl]-2-methyl-3-(4-methoxybenzoyl)-1H-indole hydrochloride, m.p. 219°–225° C. (from isopropanol/diethyl ether), $[\alpha]_D^{25} = -2.8°$ (1% in DMF).

Similarly, reaction of 10.5 g. (0.043 mole) of (d)-1-(4-methyl-2-morpholinyl)methyl]-2-methyl-1H-indole (Preparation 1A) with 14.2 ml. (0.086 mole) of 4-methoxybenzoyl chloride in MDC in the presence of 14.3 g. (0.108 mole) of aluminum chloride and isolation of the product in the form of the hydrochloride salt afforded 3.9 g. of (d)-1-(4-methyl-2-morpholinyl)methyl]-2-methyl-3-(4-methoxybenzoyl)-1H-indole hydrochloride as dimorphic crystals, m.p. 151°–159° C. and 219°–221° C. (from ethanol/diethyl ether), $[\alpha]_D^{25} = +3.1°$ (1% in DMF).

Following a procedure similar to that described in Example 1A above, the following compounds of Formula I in Table 1 were similarly prepared.

TABLE 1

| Ex. | $R_3$ | $R_2/R_4$ | (Alk)/Het | Base/Salt | m.p./solv. |
|---|---|---|---|---|---|
| 1B | 4-CH$_3$OC$_6$H$_4$ | CH$_3$ | — | HCl | 256–259.5 |
|    |                     | H       | 1-CH$_3$-4-pip. |     | EtOH |
| 1C | C$_6$H$_5$ | CH$_3$ | CH$_2$ | HCl | 258–259 |
|    |            | H      | 4-CH$_3$-2-mor. |    | MeOH |
| 1D | 4-HOC$_6$H$_4$ | CH$_3$ | CH$_2$ | base | 227–228 |
|    |                 | H      | 4-CH$_3$-2-mor. |      | CH$_3$CN |
| 1E | 3-CH$_3$OC$_6$H$_4$ | CH$_3$ | CH$_2$ | salt (a) | 148–150 |
|    |                     | H      | 4-CH$_3$-2-mor. |          | acetone |
| 1F | 2-FC$_6$H$_4$ | CH$_3$ | CH$_2$ | HCl (b) | 247–248 |
|    |               | H      | 4-CH$_3$-2-mor. |         | CH$_3$CN |
| 1G | 1-naphthyl | CH$_3$ | CH$_2$ | maleate | 134–136 |
|    |            | H      | 4-CH$_3$-2-mor. |         | EtOAc |
| 1H | 4-CH$_3$OC$_6$H$_4$ | H | CH$_2$ | base | 118–120 |
|    |                     | 5-F | 1-CH$_3$-3-pip. |      | MDC/Et$_2$O |
| 1I | 4-CH$_3$OC$_6$H$_4$ | H | CH$_2$ | base | 137–139 |
|    |                     | H | 1-CH$_3$-3-pip. |      | EtOAc/Hex. |
| 1J | 2-FC$_6$H$_4$ | CH$_3$ | CH$_2$ | maleate | 112–114 |
|    |               | H      | 1-CH$_3$-3-pip. |         | EtOAc |
| 1K | C$_6$H$_5$ | CH$_3$ | CH$_2$ | HCl | 266–267 |
|    |            | H      | 1-CH$_3$-3-pip. |     | EtOH/Et$_2$O |
| 1L | 4-ClC$_6$H$_4$ | CH$_3$ | CH$_2$ | HCl | 260–261 |
|    |                | H      | 1-CH$_3$-3-pip. |     |  |
| 1M | 1-naphthyl | CH$_3$ | CH$_2$ | HCl | 185–186 |
|    |            | H      | 1-CH$_3$-3-pip. |     | Tol./Et$_2$O |
| 1N | 4-CH$_3$OC$_6$H$_4$ | H | CH$_2$ | base | 101–102 |
|    |                     | H | 1-CH$_3$-3-pip. |      | t-Bu-O-Me |
| 1O | 3-FC$_6$H$_4$ | CH$_3$ | CH$_2$ | HCl | 242–243 |
|    |               | H      | 1-CH$_3$-3-pip. |     | EtOAc/Et$_2$O |
| 1P | 1-naphthyl | H | CH$_2$ | HCl.¼ H$_2$O | 175–176 |
|    |            | H | 1-CH$_3$-3-pip. |              | Tol./Et$_2$O |
| 1Q | C$_6$H$_5$ | H | CH$_2$ | CH$_3$SO$_3$H | 93–94 |
|    |            | H | 1-CH$_3$-3-pip. | H$_2$O | i-PrOH/Et$_2$O |
| 1R | 1-naphthyl | H | — | base | 106–107 |
|    |            | H | 1-CH$_3$-3-azep. (c) |      | i-PrOH/MDC |
| 1S | 4-CH$_3$OC$_6$H$_4$ | (CH$_3$)$_2$CH | CH$_2$ | HCl | 249–251 |
|    |                     | 5-F            | 1-CH$_3$-3-pip. |     | MeOH/Et$_2$O |
| 1T | 3-CH$_3$OC$_6$H$_4$ | CH$_3$ | CH$_2$ | HCl.¼ H$_2$O | 122–123 |
|    |                     | H      | 1-CH$_3$-3-pip. |              | i-PrOH/Et$_2$O |

TABLE 1-continued

| Ex. | R$_3$ | R$_2$/R$_4$ | (Alk)/Het | Base/Salt | m.p./solv. |
|---|---|---|---|---|---|
| 1U | 4-CH$_3$OC$_6$H$_4$ | (CH$_3$)$_2$CH<br>H | CH$_2$<br>1-CH$_3$-3-pip. | HCl.¼ H$_2$O | 119–122<br>(d) |
| 1V | 4-CH$_3$SC$_6$H$_4$ | CH$_3$<br>H | CH$_2$<br>1-CH$_3$-2-pyrd. | base | 109–110<br>Et$_3$N |
| 1W | 4-CH$_3$OC$_6$H$_4$ | CH$_3$<br>H | —<br>1-Bzl-3-pyrd. | Tosylate<br>¾ H$_2$O | 125–130 |
| 1X | 4-CH$_3$OC$_6$H$_4$ | CH$_3$<br>H | —<br>1-Me-3-pyrd. | base | 55–65 |
| 1Y | 4-CH$_3$OC$_6$H$_4$ | CH$_3$<br>H | CH$_2$<br>1,2-di-CH$_3$-5-pyrd. (e) | base | 112–116<br>CH$_3$CN |
| 1Z | 4-CH$_3$OC$_6$H$_4$ | CH$_3$<br>H | CH$_2$<br>1,2-di-CH$_3$-5-pyrd. (f) | HCl | 237–241<br>i-PrOH/Et$_2$O |
| 1AA | 4-CH$_3$OC$_6$H$_4$ | H<br>H | CHCH$_3$<br>1-CH$_3$-2-pyrd. (g) | HCl.¼ H$_2$O | 159–161<br>EtOAc/Et$_2$O |
| 1AB | 4-CH$_3$OC$_6$H$_4$ | H<br>H | CHCH$_3$<br>1-CH$_3$-2-pyrd. (h) | HCl<br>3/2 H$_2$O | 153–155<br>MeOH/Et$_2$O |
| 1AC | 2-FC$_6$H$_4$ | H<br>H | CHCH$_3$<br>1-CH$_3$-2-pyrd. (h) | HCl.H$_2$O | 137–139<br>MeOH/Et$_2$O |
| 1AD | 2-FC$_6$H$_4$ | CH$_3$<br>H | CH$_2$<br>1,2-di-CH$_3$-5-pyrd. (e) | HCl | 188–190<br>i-PrOH |
| 1AE | 4-CH$_3$OC$_6$H$_4$ | CH$_3$<br>H | CH$_2$<br>1-Bzl-2-CH$_3$-5-pyrd. (e) | HCl | 157–161<br>i-PrOH |
| 1AF | 4-CH$_3$OC$_6$H$_4$ | CH$_3$<br>H | CHCH$_3$<br>1-CH$_3$-2-pyrd. (h) | HCl | 240–241<br>MeOH/Et$_2$O |
| 1AG | 4-CH$_3$OC$_6$H$_4$ | CH$_3$<br>H | CH$_2$<br>1-Bzl.-2-pyrd. | Base | 93–94 |
| 1AH | 4-CH$_3$OC$_6$H$_4$ | CH$_3$<br>H | CH$_2$<br>1,5,5-(CH$_3$)$_3$-2-pyrd. | HCl | 186–189<br>i-PrOH/Et$_2$O |
| 1AI | 2-FC$_6$H$_4$ | CH$_3$<br>H | CH$_2$<br>1-Bzl.-5-CH$_3$-2-pyrd. | HCl | 231–234<br>i-PrOH |
| 1AJ | 2-FC$_6$H$_4$ | H<br>H | CH$_2$<br>1-(4-CH$_3$OBzl.)-2-pyrd. | Base | oil |

(a) Mono (cyclohexylsulfamate) hemihydrate.
(b) The maleate salt has m.p. 137–140° C., from ethyl acetate.
(c) The starting material was 1-[(1-methyl-2-pyrrolidinyl)methyl]-1H-indole, and the (1-methyl-2-pyrrolidinyl)methyl group underwent rearrangement and ring expansion under the conditions of the reaction.
(d) The product was precipitated from diethyl ether without recrystallization.
(e) trans.
(f) cis.
(g) syn.
(h) anti.

By N-Alkylation of the Compounds of Formula VI

Example 2A

To a suspension of 1.6 g. (0.041 mole) of a 60% sodium hydride in hexane dispersion in 160 ml of DMF was added 7.7 g. (0.027 mole) of 5-fluoro-2-methyl-3-(4-methoxybenzoyl)indole under a nitrogen atmosphere. The reaction mixture was stirred for one hour at room temperature, treated with a solution of 2-(2-chloroethyl)-1-methylpyrrolidine in 25 ml of DMF and stirred at room temperature for about twelve hours. The mixture was then treated with excess acetic acid, concentrated to a small volume in vacuo, treated with water and extracted with MDC. The combined organic extracts were washed with water, then with brine, dried over magnesium sulfate, filtered and taken to dryness to give 13.0 g. of the product in the form of the free base which was converted to the hydrochloride salt in ethereal hydrogen chloride. Recrystallization of the salt from methanol/ether gave 7.2 g. of 5-fluoro-2-methyl-1-[2-(1-methyl-2-pyrrolidinyl)ethyl]-3-(4-methoxybenzoyl)-1H-indole hydrochloride hemihydrate, m.p. 145°–147° C. The anhydrous monohydrochloride shows m.p. 154°–156° C. (from methanol/ethyl acetate).

Following a procedure similar to that described in Example 2A above, the following compounds of Formula I in Table 2 were similarly prepared.

TABLE 2

| Ex. | R$_3$ | R$_2$/R$_4$ | (Alk)/Het | Base/Salt | m.p./solv. |
|---|---|---|---|---|---|
| 2B | 4-CH$_3$OC$_6$H$_4$ | CH$_3$<br>H | CH$_2$CH$_2$<br>1-CH$_3$-2-pyrd. | HCl.¼H$_2$O<br>(a) | 125–127<br>i-PrOH |
| 2C | 4-CH$_3$OC$_6$H$_4$ | H<br>5-F | CH$_2$CH$_2$<br>1-CH$_3$-2-pyrd. | HCl.¼H$_2$O<br>(b) | 168–170<br>MDC/Et$_2$O |
| 2D | 4-CH$_3$OC$_6$H$_4$ | CH$_3$<br>H | CH$_2$<br>1-CH$_3$-3-pip. | base<br>(c) | 91.5–93.5<br>EtOAc/Hex. |
| 2E | 4-CH$_3$OC$_6$H$_4$ | CH$_3$<br>H | CH$_2$<br>1-CH$_3$-2-pyrd. | HCl<br>(d) | 235.5–237.5<br>MeOH/i-PrOH |
| 2F | 4-CH$_3$OC$_6$H$_4$ | H<br>H | CH$_2$CH$_2$<br>1-CH$_3$-2-pip. | base | 97–98<br>(e) |
| 2G | 4-CH$_3$OC$_6$H$_4$ | CH$_3$<br>H | CH$_2$CH$_2$<br>1-CH$_3$-2-pip. | HCl.¼H$_2$O | 120–121<br>EtOH/Et$_2$O |
| 2H | 4-CH$_3$OC$_6$H$_4$ | CH$_3$<br>H | CH$_2$<br>1-CH$_3$-2-pip. | HCl<br>(f) | 288–289<br>EtOAc |
| 2I | 4-CH$_3$OC$_6$H$_4$ | CH$_3$<br>5-F | CH$_2$<br>1-CH$_3$-3-pip. | base<br>(g) | 112–120<br>CH$_3$CN |
| 2J | 4-CH$_3$OC$_6$H$_4$ | H<br>H | CH$_2$<br>1-CH$_3$-2-pip. | base | 159–160<br>(e) |

TABLE 2-continued

| Ex. | R$_3$ | R$_2$/R$_4$ | (Alk)/Het | Base/Salt | m.p./solv. |
|---|---|---|---|---|---|
| 2K | 4-CH$_3$OC$_6$H$_4$ | C$_2$H$_5$ | CH$_2$ | HCl | 216-217 |
|   |   | H | 1-CH$_3$-3-pip. |   | i-PrOH |
| 2L | 4-CH$_3$OC$_6$H$_4$ | CH$_3$ | CH$_2$ | HCl.½H$_2$O | 153-154 |
|   |   | H | 1-C$_2$H$_5$-3-pip. |   | EtOH/Et$_2$O |
| 2M | 2-FC$_6$H$_4$ | H | CH$_2$ | base | 118-126 |
|   |   | H | 1-CH$_3$-2-pyrd. |   | cyclohex. |
| 2N | 4-C$_2$H$_5$C$_6$H$_4$ | CH$_3$ | CH$_2$ | HCl | 247.5-249.5 |
|   |   | H | 1-CH$_3$-3-pip. |   | MeOH/i-PrOH |
| 2O | 4-CH$_3$SC$_6$H$_4$ | CH$_3$ | CH$_2$ | HCl | 241.5-245.5 |
|   |   | H | 1-CH$_3$-3-pip. |   | EtOH/Et$_2$O |
| 2P | 1-naphthyl | H | CH$_2$ | base | 134.5-136.5 |
|   |   | H | 1-CH$_3$-2-pip. |   |   |
| 2Q | 1-naphthyl | CH$_3$ | CH$_2$ | base | 110.5-112.5 |
|   |   | H | 1-CH$_3$-2-pyrd. |   | Hex. |
| 2R | 1-naphthyl | CH$_3$ | CH$_2$ | base | 140-141 |
|   |   | H | 1-CH$_3$-2-pip. |   | Cyclohex. |
| 2S | 4-CH$_3$OC$_6$H$_4$ | H | CH$_2$CH$_2$ | base | 93-97 |
|   |   | H | 1-CH$_3$-2-pyrd. |   | EtOAc |
| 2T | 4-CH$_3$OC$_6$H$_4$ | CH$_3$ | CH$_2$ | HCl.½H$_2$O | 138-140 |
|   |   | H | 1-Bzl-3-pip. |   | i-PrOH/Et$_2$O |
| 2U | 1-naphthyl | H | CH$_2$CH$_2$ | base | 136-138 |
|   |   | H | 1-CH$_3$-2-pip. |   | CH$_3$CN |
| 2V | 4-CH$_3$OC$_6$H$_4$ | CH$_3$ | CH$_2$ | base | 128-131 |
|   |   | H | 1,4-di-CH$_3$-2-pzl. |   | CH$_3$CN |
| 2W | 4-CH$_3$OC$_6$H$_4$ | H | CH$_2$ | HCl.½H$_2$O | 106-107 |
|   |   | H | 1-CH$_3$-2-pyrd. |   | i-PrOH/Et$_2$O |
| 2X | 4-CH$_3$OC$_6$H$_4$ | CH$_3$ | — | HCl.½H$_2$O | 160-162 |
|   |   | H | 1-CH$_3$-3-azep. (h) |   | i-PrOH/Et$_2$O |
| 2Y | 4-CH$_3$OC$_6$H$_4$ | CH$_3$ | CH$_2$ | HCl.½H$_2$O | 200-201 |
|   |   | H | 1-C$_2$H$_5$-2-pyrd. (i) |   | i-PrOH/Et$_2$O |
| 2Z | 1-naphthyl | H | — | base.¼H$_2$O | 69-75 |
|   |   | H | 1-CH$_3$-3-azep. (j) |   |   |
| 2AA | 2-FC$_6$H$_4$ | H | CH$_2$ | base | 101-103 |
|   |   | H | 1-CH$_3$-3-pip. |   | Cyclohex. |
| 2AB | 1-naphthyl | CH$_3$ | — | HCl.½H$_2$O | 190-191 |
|   |   | H | 1-CH$_3$-3-azep. (j) |   | i-PrOH/Et$_2$O |
| 2AC | 2-FC$_6$H$_4$ | H | CH$_2$ | base | 119-121 |
|   |   | H | 1-CH$_3$-2-pip. |   | Hex./EtOAc |
| 2AD | 2-FC$_6$H$_4$ | H | — | HCl.½H$_2$O | 140-145 |
|   |   | H | 1-CH$_3$-3-azep. (j) |   |   |
| 2AE | 4-CH$_3$OC$_6$H$_4$ | CH$_3$ | — | HCl.¾H$_2$O | 151-152 |
|   |   | H | 1-C$_2$H$_5$-3-pip. |   | i-PrOH/Et$_2$O |
| 2AF | 4-CH$_3$OC$_6$H$_4$ | CH$_3$ | CH$_2$ | HCl.¼H$_2$O | 224-225 |
|   |   | H | 1-CH$_3$-3-(4H-pyd.) |   | i-PrOH |
| 2AG (a) | 4-CH$_3$OC$_6$H$_4$ | CH$_3$ | — | HCl.½H$_2$O | 150-154 |
|   |   | H | 1-CH$_3$-3-pip. (k) |   | EtOAc/Et$_2$O |
| 2AG (b) | 4-CH$_3$OC$_6$H$_4$ | CH$_3$ | — | HCl.½H$_2$O | 152-155 |
|   |   | H | 1-CH$_3$-3-pip. (k) |   | Et$_2$O |
| 2AH | 4-CH$_3$OC$_6$H$_4$ | CH$_3$ | CH$_2$ | base | 147-149 |
|   |   | H | 1-CH$_3$-4-pip. |   | CH$_3$CN |
| 2AI | 4-CH$_3$OC$_6$H$_4$ | CH$_3$ | CH$_2$ | HCl.½H$_2$O | 122-123 |
|   |   | H | 1-CH$_3$-3-pyrd. | (l) | i-PrOH/Et$_2$O |
| 2AJ | 2-FC$_6$H$_4$ | CH$_3$ | CH$_2$ | HCl | 217-218 |
|   |   | H | 1-CH$_3$-2-pyrd. |   | EtOH/Et$_2$O |
| 2AK | 4-C$_2$H$_5$C$_6$H$_4$ | CH$_3$ | CH$_2$ | HCl.½H$_2$O | 154-155 |
|   |   | H | 1-CH$_3$-2-pyrd. |   | EtOH/Et$_2$O |
| 2AL | 4-CH$_3$OC$_6$H$_4$ | CH$_3$ | CH$_2$ | base | 156-158 |
|   |   | H | 1-Bzhyd.-3-azet. |   | Et$_2$O |
| 2AM | 1-naphthyl | H | CH$_2$ | HCl | 159-162 |
|   |   | H | 1-Bzl-2-pip. |   | MeOH/EtOH |
| 2AN | 4-NO$_2$C$_6$H$_4$ | CH$_3$ | CH$_2$ | HCl | 230-231 |
|   |   | H | 1-CH$_3$-3-pip. |   | i-PrOH/Et$_2$O |
| 2AO | 1-naphthyl | H | — | HCl | 135-137 |

TABLE 2-continued

| Ex. | R₃ | R₂/R₄ | (Alk)/Het | Base/Salt | m.p./solv. |
|---|---|---|---|---|---|
| | | H | 1-Bzl.-3-azep. | | MeOH/Et₂O |

(a) The free base has m.p. 84-85° C. (from acetonitrile).
(b) The unhydrated hydrochloride, recrystallized from MDC/methanol/diethyl ether, also has m.p. 168-170° C.
(c) The hydrochloride salt has m.p. 229-232° C. (from ethanol).
(d) The maleate salt has m.p. 153-154° C. (from acetonitrile). Reaction of (l)-1-methyl-2-hydroxymethylpyrrolidine ($[\alpha]_D^{25} = -47.7°$ C.) and (d)-1-methyl-2-hydroxymethylpyrrolidine ($[\alpha]_D^{25} = +50.1°$) with thionyl chloride in MDC afforded the corresponding (l)- and (d)-1-methyl-2-chloromethylpyrrolidines. The latter, on reaction with 2-methyl-3-(4-methoxybenzoyl)indole in DMF in the presence of potassium carbonate and isolation of the products in the form of the hydrochloride salts, afforded (l)-1-(1-methyl-2-pyrrolidinylmethyl)-2-methyl-3-(4-methoxybenzoyl)-1H-indole hydrochloride, m.p. 235-238° C. (from methanol/ether), $[\alpha]_D^{25} = -7.4°$ (methanol) and (d)-1-(1-methyl-2-pyrrolidinylmethyl)-2-methyl-3-(4-methoxybenzoyl)-1H-indole hydrochloride, m.p. 235-238° C. (from methanol/ether), $[\alpha]_D^{25} = +7.7°$ (methanol).
(e) Solid crystallized from an oil and not recrystallized.
(f) The free base, purified by chromatography on silica gel, eluting with 1:1 hexane:ethyl acetate and recrystallization from acetone, has m.p. 122-123° C.
(g) The hydrochloride has m.p. 247-249° C. (from ethanol/ether).
(h) The starting alkylating agent was 1-methyl-3-chloromethylpiperidine hydrochloride which underwent rearrangement with ring expansion during the reaction.
(i) The starting alkylating agent was 1-ethyl-3-chloropiperidine hydrochloride which underwent rearrangement with ring contraction during the reaction.
(j) The starting alkylating agent was 1-methyl-2-chloromethylpiperidine hydrochloride which underwent rearrangement with ring expansion during the reaction.
(k) The products of Examples 2AG (a) and 2AG (b) are the d- and l-enantiomers, respectively, having $[\alpha]_D^{25} = +3.1°$ (methanol) and $[\alpha]_D^{25} = -2.4°$ (methanol), respectively, and were isolated as by-products of the reactions in Example 2E using (d)- and (l)-1-methyl-2-chloromethylpyrrolidines as alkylating agents, which thus underwent rearrangement, with ring expansion and retention of stereo configuration, during the reaction. See Example 4A for racemic form.
(l) The hydrochloride monohydrate has m.p. 115-116° C. (from isopropanol/ether).

By Replacement of an N-Lower-alkylsulfonyl Group in a Compound of Formula VII

Proceeding in a manner similar to that described in Example 3A above, the following compounds in Table 3 were similarly prepared.

TABLE 3

| Ex. | R₃ | R₂/R₄ | (Alk)/Het | Base/Salt | m.p./solv. |
|---|---|---|---|---|---|
| 3B | 4-CH₃OC₆H₄ | CH₃ | — | maleate | 172.5-174 |
| | | H | 5-CH₃-3-thiaz. (a) | | EtOH |
| 3C | 4-CH₃OC₆H₄ | CH₃ | CH₂ | base | 124-126 |
| | | H | 4-CH₃-2-thiom. | | CH₃CN |
| 3D | 4-CH₃OC₆H₄ | CH₃ | CH₂ | HCl | 186-188 |
| | | H | 4-Bzl.-3-mor. | | i-PrOH/Et₂O |
| 3E | 4-CH₃OC₆H₄ | CH₃ | CH₂ | base | 137-139 |
| | | H | 1-CH₃-2-ind. | | EtOAc/Hex |
| 3F | 1-naphthyl | H | CH₂ | base | 75-78 |
| | | H | 4-Bzl.-3-mor. | | |
| 3G | 1-naphthyl | H | CH₂ | base (b) | 68-75 |
| | | H | 1,4-di-CH₃-pzl. | | |

(a) The product was obtained as a by-product of Example 3A in which the starting alkylating agent, 3-hydroxymethyl-4-methylthiomorpholine, underwent rearrangement during the reaction.
(b) The mono p-toluenesulfonate quaternary salt, 1.0 g., m.p. 220.0-222.0, was prepared by reaction of 1.0 g. of the free base from Example 3G with 0.45 g. of methyl p-toluenesulfonate in 5 ml. of acetone and the product collected, triturated with chloroform/ether and dried.

Example 3A

To a solution of 8.82 g. (0.06 mole) of 3-hydroxymethyl-4-methylthiomorpholine in 500 ml. of toluene was added 1.44 g. (0.06 mole) 97% sodium hydride under nitrogen at 0° C. The mixture was stirred for thirty minutes, allowed to warm to room temperature, heated to reflux and treated with 17.15 g. (0.05 mole) of 1-methanesulfonyl-2-methyl-3-(4-methoxybenzoyl)-1H-indole. After three hours it was cooled and treated with ice. The reaction mixture was partitioned between ethyl acetate and water, the organic layer was separated, and the aqueous layer extracted with additional ethyl acetate. The combined organic extracts were washed with water, dried over magnesium sulfate and taken to dryness in vacuo to give a thick oil which solidified. The oil was taken into toluene and chromatographed on silica gel, eluting initially with 50% ethyl acetate/hexane to remove unreacted starting material and then with ethyl acetate alone to remove the products. There was thus obtained 11.51 g. of crude product which was recrystalized from acetone to give 10.68 g. of 1-[(4-methyl-3-thiomorpholinyl)methyl]-2-methyl-3-(4-methoxybenzoyl)-1H-indole, m.p. 127.5°-127° C.

By Catalytic Reduction of a 1-Heteroaryl Group

Example 4A

A solution of 15.8 g. (0.03 mole) of 1-(1-methyl-3-pyridinium)-2-methyl-3-(4-methoxybenzoyl)-1H-indole p-toluene-sulfonate in 250 ml of ethanol containing 3 ml of concentrated hydrochloric acid was reduced in a Parr shaker over 1 g. of platinum oxide catalyst at room temperature under an initial hydrogen pressure of 50 pounds p.s.i.g. When hydrogen uptake ceased, the catalyst was removed by filtration, an additional 1.0 g. of fresh catalyst was added, and hydrogenation was continued with heating. When reduction was complete, the catalyst was again removed by filtration and the filtrate taken to dryness in vacuo to give 17 g. of a yellow oil which was chromatographed on silica gel, eluting with 3:1 ethyl acetate:acetone, the product being collected as the late fractions. The crude product thus obtained was converted to the hydrochloride salt and the latter recrystallized from isopropanol to give 4.6 g. of 1-(1-methyl-3-piperidinyl)-2-methyl-3-(4-methoxybenzoyl)-1H-indole hydrochloride, m.p. 190°-193° C.

Following a procedure similar to that described in Example 4A above, the following compounds of Formula I given in Table 4 were similarly prepared.

10.9 g. of 1-[(1-methyl-3-piperidinyl)-methyl]-2-methyl-3-(4-methylsulfinylbenzoyl)-1H-indole hydrochloride, m.p. 245°–256° C.

TABLE 4

| Ex. | R$_3$ | R$_2$/R$_4$ | (Alk)/Het | Base/Salt | m.p./solv. |
|---|---|---|---|---|---|
| 4B | 4-CH$_3$OC$_6$H$_4$ | CH$_3$ | CH$_2$ | HCl.C$_2$H$_5$OH | 140–143 |
|    |                      | H     | 3-pip.          | (a)             | EtOH |
| 4C | 4-CH$_3$OC$_6$H$_4$ | CH$_3$ | CH$_2$ | base | 173–174 |
|    |                      | H     | 2-pzl.          |                 | CH$_3$CN |
| 4D | 2-FC$_6$H$_4$       | H     | —               | HCl             | 234–238 |
|    |                      | H     | 1-CH$_3$-3-pip. |                 | EtOH |
| 4E | 2-FC$_6$H$_4$       | H     | CH$_3$CH        | HCl             | 154–164 |
|    |                      | H     | 3-pip.          | (b)             | i-PrOH/Et$_2$O |
| 4F | 2-FC$_6$H$_4$       | H     | CH$_3$CH        | base            | 98.5–100.5 |
|    |                      | H     | 1-CH$_3$-3-pip. | (b)             | i-PrOH |
| 4G | 2-FC$_6$H$_4$       | H     | CH$_3$CH        | HCl.¼ H$_2$O    | 140–175 |
|    |                      | H     | 1-CH$_3$-3-pip. | (c)             | i-PrOH/Et$_2$O |
| 4H | 2-FC$_6$H$_4$       | H     | CH$_3$CH        | HCl.¼ H$_2$O    | 216–219 |
|    |                      | H     | 3-pip.          | (c)             | i-PrOH/Et$_2$O |
| 4I | 1-naphthyl           | H     | CH$_2$          | HCl             | 282–284 |
|    |                      | H     | 2-pip.          |                 | EtOH/Et$_2$O |

(a) The hydrochloride ¼ H$_2$O has m.p. 150–151° C. (from ethanol).
(b) Anti isomer (See Example 4E).
(c) Syn isomer (See Example 4F).

By Replacement of a Trimethylsilyl Group

Example 5

A solution of 36 g. (0.10 mole) of 2-methyl-3-(4-methoxybenzoyl)-1-trimethylsilylmethyl-1H-indole in 700 ml of diethylene glycol dimethyl ether was treated with 15 ml (0.12 mole) of 1-methyl-4-oxopiperidine, the reaction flask was flushed with nitrogen, 10 ml of 3A° molecular sieves were added, the reaction mixture was stirred for fifteen minutes, treated with 17 g. (0.11 mole) of cesium fluoride and the reaction mixture heated at 80°–100° C. for about twelve hours and then taken to dryness in vacuo. The residue was taken into ethyl acetate, the solution filtered through filter aid and the filter washed with MDC. The combined filtrates were taken to dryness in vacuo, the residue again dissolved in ethyl acetate and the solution extracted with 1N hydrochloric acid. The combined aqueous extracts were washed with ethyl acetate, basified with sodium hydroxide and extracted with ethyl acetate and the combined organic extracts were dried over sodium sulfate and taken to dryness. The resulting residue was slurried with ethyl acetate/acetone and the resulting solid collected and dried to give 0.9 g. of 2-methyl-3-(4-methoxybenzoyl)-1-[(1-methyl-4-hydroxy-4-piperidinyl)methyl]-1H-indole, m.p. 138°–140° C.

Miscellaneous Processes

Example 6A

A solution of 17.1 g. (0.04 mole) of 1-[(1-methyl-3-piperidinyl)methyl]-2-methyl-3-(4-methylmercaptobenzoyl)-1H-indole hydrochloride in 200 ml of chloroform was treated with a solution of 10 g. (0.046 mole) of m-chloroperbenzoic acid in 100 ml. of chloroform while cooling in a methanol/ice bath. The resulting mixture was stirred for one hour, allowed to stand at room temperature for eighteen hours and then taken to dryness in vacuo to give an orange oil which was partitioned between water and chloroform. The organic layer was washed with 10% sodium hydroxide, separated, dried over magnesium sulfate and taken to dryness to give 19.5 g. of a yellow orange oil which was dissolved in isopropyl alcohol and treated with concentrated hydrochloric acid. The solid which separated was collected and recrystallized from ethanol/diethyl ether to give

Example 6B

Following a procedure similar to that described in Example 6A above, 1.09 g. (0.0025 mole) of 2-methyl-3-(4-methoxybenzoyl)-1-[(4-methyl-3-thiomorpholinyl)-methyl]-1H-indole hydrochloride in 15 ml of MDC was oxidized with 423 µl of 30% hydrogen peroxide in 423 µl of hexafluoro acetone sesquihydrate and the product isolated in the form of the free base to give 1.23 g. of 2-methyl-3-(4 methoxybenzoyl)-1-[(4-methyl-3-thiomorpholinyl)methyl]-1H-indole-S-oxide, m.p. 172°–174° C. (recrystallized from acetone/chloroform).

Example 7

A solution of 3.98 g. (0.01 mole) of 2-methyl-3-(4-methoxybenzoyl)-1-[(3-piperidinyl)methyl]-1H-indole hydrochloride and 1.2 g. (0.021 mole) of propionaldehyde in 50 ml of methanol was treated with 0.63 g. (0.01 mole) of sodium cyanoborohydride, and 3 g. of 3A° molecular sieves were added. The reaction mixture was stirred for twenty-four hours in a flask protected from moisture with a drying tube, treated with an additional 0.5 ml of propionaldehyde and 0.63 g. of sodium cyanoborohydride, stirred for an additional two hours and then poured into dilute hydrochloric acid. The mixture was basified by the addition of concentrated ammonium hydroxide and then extracted with MDC. The combined organic extracts were dried over magnesium sulfate and concentrated in vacuo to give an oil which was treated with excess ethereal hydrogen chloride. The solid which separated was collected and recrystallized from acetonitrile to give 3.3 g. of 2-methyl-3-(4-methoxybenzoyl)-1-[(1-propyl-3-piperidinyl)methyl]-1H-indole hydrochloride, m.p. 225°–227° C.

Example 8A

A mixture of 3.7 g. (0.0084 mole) of 2-methyl-3-(4-methoxybenzoyl)-1-[(1-benzyl-2-pyrrolidinyl)methyl]-1H-indole, 1.0 g. of 10% palladium-on-charcoal and 50 ml of methanol was heated to reflux with stirring under a nitrogen atmosphere and then treated with 4.0 g. of ammonium formate added in portions over a period of five minutes. The reaction mixture was heated under reflux for an additional two hours, then filtered and the filtrate concentrated to a small volume in vacuo. The residue was basified with concentrated ammonium hydroxide, extracted with MDC, the combined organic extracts were dried over magnesium sulfate, evaporated to dryness, and the resulting yellow oil was dissolved in ethyl acetate and treated with ethereal hydrogen chloride. The solid which separated was recrystallized from acetonitrile/methanol to give 5.8 g. of 2-methyl-3-(4-methoxybenzoyl)-1-[(2pyrrolidinyl)methyl]-1H-indole hydrochloride, m.p. 170°–172° C.

Following a procedure similar to that described in Example 8A above, the following compounds given in Table 8 were similarly prepared.

TABLE 8

| Ex. | $R_3$ | $R_2/R_4$ | $(Alk)_n$/Het | Base/Salt | m.p./solv. |
|---|---|---|---|---|---|
| 8B | 4-CH$_3$OC$_6$H$_4$ | CH$_3$ | — | HCl.½ H$_2$O | 147–152 |
|    |                      | H       | 3-pyrd. (b) |            | EtOH/Et$_2$O |
| 8C | 4-CH$_3$OC$_6$H$_4$ | CH$_3$ | CH$_2$ | HCl | 264–266 |
|    |                      | H       | 3-mor. (a) |     | MeOH |
| 8D | 4-CH$_3$OC$_6$H$_4$ | CH$_3$ | — | HCl | 188–189 |
|    |                      | H       | 3-azep. (b) |     | EtOH |
| 8E | 2-FC$_6$H$_4$ | CH$_3$ | CH$_2$ | HCl | 254–256 |
|    |                | H       | 5-CH$_3$-2-pyrd. (a) | EtOH/Et$_2$O | |
| 8F | 3-FC$_6$H$_4$ | H | CH$_2$ | HCl | 245–246 |
|    |                | H | 2-pyrd. (c) |     | EtOH |
| 8G | 1-naphthyl | H | CH$_2$ | HCl.½ H$_2$O | 176–178 |
|    |            | H | 3-mor. (a) |              | EtOH |

(a) Reduction carried out over Pd/C in presence of ammonium formate.
(b) Starting material was corresponding N-benzhydryl compound, and reduction carried out over Pd/C only.
(c) Starting material was corresponding 4-methoxybenzyl compound (See Example 1AJ) and cleavage carried out by heating equimolar amounts of starting material and α-chloroethoxyformyl chloride in EDC.

Example 9

2-Methyl-3-(4-nitrobenzoyl)-1-[(1-methyl-3-piperidinyl)methyl]-1H-indole hydrochloride (2.0 g., 0.0046 mole) dissolved in 240 ml of ethanol was reduced with hydrogen at ambient temperature under 50 pounds p.s.i.g. in a Parr shaker over 4 g. of 10% palladium-on-charcoal. When reduction was complete, the catalyst was removed by filtration, the filtrate was taken to dryness, and the residue was dissolved in 35 ml of ethanol and diluted with diethyl ether. The solid which separated was collected and dried to give 1.2 g. of 2-methyl-3-(4-aminobenzoyl)-1-[(1-methyl-3-piperidinyl)methyl]-1H-indole hydrochloride hemihydrate, m.p. 171°–173° C.

Example 10A

A solution of 2.2 g. (0.0069 mole) of 2-methyl-3-(4-methoxybenzoyl)-1-(3-azetidinyl)-1H-indole in 38 ml of 97% formic acid and 13 ml of 35% aqueous formaldehyde was heated under reflux for two hours and then taken to dryness in vacuo. The residue was partitioned between ammonium hydroxide and ethyl acetate, the organic layer was separated and the aqueous layer extracted with additional ethyl acetate. The combined organic extracts were washed with brine, dried over magnesium sulfate, filtered and taken to dryness to give 2.0 g. of residue which was dissolved in 20 ml of isopropanol and the solution treated with a solution of 348 mg of maleic acid in 5 ml of isopropanol. The solid which separated was collected and recrystallized from isopropanol to give 0.66 g. of 2-methyl-3-(4-methoxybenzoyl)-1-(1-methyl-3-azetidinyl)-1H-indole maleate, m.p. 131°–133° C.

Example 10B

Following a procedure similar to that described in Example 10A above, 1.5 g. (0.004 mole) of 2-methyl-3-(4-methoxybenzoyl)-1-[(3-morpholinyl)methyl]-1H-indole was subjected to reductive methylation using 0.84 ml of 37% formaldehyde and 0.65 ml of 95% formic acid. The product was isolated in the form of the free base which was purified by chromatography on silica gel in chloroform, the product being eluted with 5% methanol in chloroform, to give 1.2 g. of 2-methyl-3-(4-methoxybenzoyl)-1-[(4-methyl-3-morpholinyl)methyl]-1H-indole, m.p. 125° ∝ 126° C.

Example 10C

Following a procedure similar to that described in Example 10A above, 1.25 g. of 3-(1-naphthylcarbonyl)-1-[(3-morpholinyl)methyl]-1H-indole was subjected to reductive alkylation using 758 μl of 37% formaldehyde and 513 μl 97% formic acid. The product was isolated in the form of the hydrochloride salt which was purified by recrystallization from ethanol to give 0.94 g. of 3-(1-naphthylcarbonyl(-1-[(4-methyl-3-morpholinyl)methyl]-1H-indole hydrochloride, m.p. 165°–167° C.

Example 11A

A mixture of 3.0 g. of 2-methyl-3-(4-methoxybenzoyl)-1-[(1-methyl-2-pyrrolidinyl)methyl]-1H-indole maleate and 2.2 g. (0.019 mole) of pyridine hydrochloride was heated with stirring at 210° C. for five hours, then cooled, diluted with water and poured into 2N hydrochloric acid. The mixture was basified with dilute sodium hydroxide, extracted with chloroform and the pH of the aqueous layer adjusted to about 6 with dilute hydrochloric acid and extracted with chloroform. The combined organic extracts were dried over magnesium sulfate and taken to dryness to give 0.6 g. of a yellow oil which was dissolved in isopropanol and treated with excess concentrated hydrochloric acid and diethyl ether. Recrystallization of the resulting solid from isopropanol/ether afforded 0.13 g. of 2-methyl-3-(4-hydroxybenzoyl)-1-[(1-methyl-2-pyrrolidinyl)methyl]-1H-indole hydrochloride, m.p. 282°–284° C.

Example 11B

Following a procedure similar to that described in Example 11A above, 1.5 g. (0.004 mole) of 2-methyl-3-(4-methoxybenzoyl)-1-[(1,5-dimethyl-2-pyrrolidinyl)methyl]-1H-indole was cleaved with 2.77 g. (0.024 mole) of pyridine hydrochloride at 210° C. and the product isolated in the form of the hydrochloride salt to give 0.91 g. of 2-methyl-3-(4-hydroxybenzoyl)-1-[(1,5- dimethyl-2-pyrrolidinyl)methyl]-1H-indole hydrochloride, m.p. 274°-275° C. (from methanol/diethyl ether).

BIOLOGICAL TEST RESULTS

Data obtained with the compounds of the invention in the acetylcholine-induced abdominal constriction test (ACH) (expressed as the $ED_{50}$ in mg/kg or as the percent inhibition at a given dose level), the anti-bradykinin test (BDK) (expressed as the $ED_{50}$ or as the percent inhibition at a given dose level), the acetic acid-induced writhing assay in the rat (RW) (expressed as the $ED_{50}$ or the percent inhibition at a given dose level) and the Randall-Sellitto (RS) paw pressure test (expressed as the minimum effective dose, MED, in mg/kg $ED_{50}$) are given in the table below. Data in the developing adjuvant arthritis (AA) and plasma fibronectin (FN) assays are expressed as percent inhibition, i.e. inhibition of non-injected paw inflammation (NIP) and injected paw (RPV) and lowering of plasma fibronectin, the asterisks * and ** indicating statistical significance at the $p<0.01$ and $p<0.05$ levels, respectively. Compounds are considered active at $p<0.05$ level. Non-statistically significant results are recorded as "—". In the acetylcholine-induced abdominal constriction test, the test compounds were administered either as suspensions in gum tragacanth (GT) or as aqueous solutions prepared by addition of just sufficient dilute aqueous methanesulfonic acid (MS) or dilute aqueous lactic acid (LA) to dissolve the compound. The compounds are identified by the example number above where their preparations are described. All data in the anti-bradykinin, rat writhing and Randall-Selitto tests were obtained on oral administration. The abbreviations IA and Depr. represent, respectively, inactive and depressant.

TABLE 9

| Ex. | ACH | BDK | RW | NIP | RPV | RS |
|---|---|---|---|---|---|---|
| 1A (HCl) | 9 | | 3 | | | |
| 1B | 69 | | | 88* | 65* | |
| 1C | 21 | | 10 | | | |
| 1D | 10%/100 | | | | | |
| 1F | 22 | | 26 | | | |
| 1G | 10%/100 6 (iv) | | | | | |
| 1H | 20%/100 | | | 92* | 63* | |
| 1I | 38 (MS) 5 (iv) | | 32 | 61* | 19** | |
| 1J | 32 | | 45 | 61*, 59* | 52*, 40* | |
| 1K | 33 | | 40 | 76* | 50* | |
| 1L | 62 | | | 83* | 60* | |
| 1M | 25%/100 7 (iv) | | | | | 0.1 |
| 1N | 91 | | 28.3 | | | |
| 1O | 71 | | | | | |
| 1P | 144 | | | 38* | 43* | |
| 1Q | 45 | | | | | |
| 1R | 20%/100 | | | | | |
| 1S | 21 | | | 73* | 36* | |
| 1T | 64 | | | | | |
| 1U | 22 | | | | | |
| 1V | 25 | | 7 | | | |
| 1W | 35%/100 | | | | | |
| 1X | 20 | | 12 | — | 23* | |
| 1Y | 21 10 (sc) 2 (iv) | | 3 | 67* | 48* | |
| 1Z | 14 3 (iv) | | | | | |
| 1AA | 23 5 (iv) | | 20 | | | |
| 1AB | 19 | | 10 | | | |
| 1AC | 40%/100 | | | | | |
| 1AD | 34 | | | | | |
| 1AE | 30%/100 | | | | | |

TABLE 9-continued

| Ex. | ACH | BDK | RW | NIP | RPV | RS |
|---|---|---|---|---|---|---|
| 1AF | 19 | | | | | |
| 1AG | 0%/100 | | | | | |
| 2A | 32 | | | 86* | 69* | |
| 2B (HCl) | 32, 23 8 (iv) | | 25 | 69* 67* | 52* 49* | 10 |
| 2C | 49 | | | 55* | 27* | |
| 2D (base) | 8 | 2.4 | 2 | 99* | 78* | |
| 2E (d, l) | 27 6 (iv) | 35 (sc) IA (po) | 6 | — | 24* | 0.03 |
| 2E (d) | 47, 36 | | 30 | | | |
| 2E (l) | 35 | | 13 | | | |
| 2F | 45 4 (iv) | | | 50* — | 21* 15* | 3 |
| 2G | 26 | | 3 | 93* | 73* | |
| 2H (HCl) | 33 | | 22 | 69* | 51* | |
| 2I (base) | 40 | | 5 | 70* | 51* | |
| 2J | 6 (Depr.) | | 0.5 | 66* | 27* | |
| 2K | 16 11 (iv) 10 (sc) | | 23 | 68* | 54* | |
| 2L | 11 | | 2 | | | |
| 2M | 53 | | | | | |
| 2N | 46 | | | | | |
| 2O | 8 | | 5 | 65* | 44* | |
| 2P | 9 (Depr.) 0.03, 0.05 (iv) | | 98%/30 | | | |
| 2Q | 20%/100 | | | | | |
| 2R | 22 | | 100%/30 | | 57* | 29* |
| 2S | 50 | | | 33* | 21* | |
| 2T | 20%/300 | | | 92* | 68* | |
| 2U | 30%/100 | | 50%/30 | — | — | |
| 2V | 20 | | 15 | | | |
| 2W | 11 (Depr.) | | 3 | | | |
| 2X | 29 | | 82%/100 54/30 | 43* | — | |
| 2Y | 43 | | | 46* | 15** | |
| 2Z | 20%/100 80%/30 (iv) | | | | | |
| 2AA | 65 | | | 65* | — | |
| 2AB | 30%/100 | | | | | |
| 2AC | 10 (Depr.) | | | | | |
| 2AD | 20%/100 | | | — | — | |
| 2AE | 26 | | 15%/30 | | | |
| 2AF | 11 | | 15 | 93* | 78* | |
| 2AG (l) | 30 | | | | | |
| 2AG (d) | 22 | | 9 | | | |
| 2AH | 4,5 | 30%/3 | 74%/30 | | | |
| 2AI | 11,13 | | 4 | | | |
| 2AJ | 72 | | 6 | 31* | — | |
| 2AK | 40 | | 7 | — | — | |
| 2AL | 20%/100 | | | | | |
| 2AN | 30%/100 | | | | | |
| 3A | 33 | | 13 | | | |
| 3B | 60%/100 | | | | | |
| 3C | 30 | | | | | |
| 3F | 2.2 (iv) | | | | | |
| 4A (d,l) | 33 | | 57%/17 | 50* | 26* | |
| 4B | 15 | | 10 | 91* | 79* | |
| 4C | 22 | | 20 | | | |
| 4D | 65%/100 50%/30 | | | 80* | — | |
| 4E | 43 | | | | | |
| 4F | 24 | | 6 | 45* | 27* | |
| 4G | 19 | | 7 | | | |
| 4H | 25 | | 4 | | | |
| 4I | 30%/30 | | | | | |
| 5 | 23 | | 9.1 | | | |
| 6A | 9 | | 5 | 93* | 81* | |
| 6B | 5 | | | | | |
| 7 | 18 | | | | | |
| 8A | 41 | | 25 | | | |
| 8B | 29 | | | | | |
| 8G | 100%/30 | | | | | |
| 9 | 12 | | 9 | | | |
| 10A | 40 | | | | | |
| 10B | 29 | | | | | |
| 10C | 50%/30 | | | | | |

Certain species of formula II described above have been found to be active in the acetylcholine-induced abdominal constriction test. Data so obtained are given in Table 10 as follows:

TABLE 10

| Prepn. No. | ACH |
|---|---|
| 1A (a) | 10%/100 |
| 1D | 65 |
| 1P | 66 (p.o.) |
|  | 9.7 (i.v.) |
| 1Q | 30%/100 |

(a) Racemic p-toluenesulfonate

Certain species within the ambit of Formula I of the invention, as more precisely defined above, have also been found to be active in the mouse vas deferens test and in the CP 55940 binding assay compounds are considered active in the MVD test at $IC_{50}$ levels of 5.0 µM or less. Data so-obtained, expressed as the $IC_{50}$, are given in Table 11 below:

TABLE 11

| Ex. | MVD | CP |
|---|---|---|
| 1G | 0.05 |  |
| 1M | 0.091 |  |
| 1N | 0.094 |  |
| 1P | 0.028 |  |
| 1V | 0.130 |  |
| 1X | 0.150 |  |
| 1Y | 0.052 |  |
| 1Z | 0.048 |  |
| 1AA | 0.127 |  |
| 1AB | 0.56 |  |
| 1AC | 0.111 |  |
| 1AF | 0.542 |  |
| 1AH | 0.330 |  |
| 2E | 0.063 |  |
| 2H | 0.134 |  |
| 2J | 0.003 |  |
| 2M | 0.039 |  |
| 2P | 0.00022 | 1.4 |
| 2Q | 0.002 |  |
| 2R | 0.001 |  |
| 2U | 0.107 |  |
| 2W | 0.008 |  |
| 2Z | 0.082 |  |
| 2AB | 0.013 |  |
| 2AC | 0.003 |  |
| 2AK | 0.025 |  |
| 2AM | 0.051 |  |
| 2AO | 0.48 |  |
| 3F | 0.224 |  |
| 3G (base) | 0.015 | 92%/1 µM |
| 3G (quaternary) | 0.156 | 45%/1 µM |
| 4A | 0.65 |  |
| 4I | 0.0003 |  |
| 8E | 0.160 |  |
| 8F | 0.325 |  |
| 8G | 0.0047 |  |
| 10A | 0.495 |  |
| 10C | 0.0004 |  |
| 11A | 0.284 |  |
| 11B | 0.217 |  |

We claim:

1. A member of the group consisting of (A) compounds having the formula:

[Structural formula: indole-based compound with $(R_4)_m$ on benzene ring, $CO-R_3$ at 3-position, $R_2$ at 2-position, and $(Alk)_n$-Het on N]

where:
$R_2$ is hydrogen or lower-alkyl;
$R_3$ is phenyl (or phenyl substituted by from one to two substituents selected from halogen, lower-alkoxy, hydroxy, lower-alkyl, nitro, amino, lower-alkylamino, di-lower-alkylamino, lower-alkylmercapto, lower-alkylsulfinyl, lower-alkylsulfonyl and methylenedioxy), 2- or 4-biphenyl of 1- or 2-naphthyl (or 1- or 2-naphthyl substituted by from one to two substituents selected from lower-alkyl, lower-alkoxy, halogen, lower-alkylmercapto, lower-alkylsulfinyl, lower-alkylsulfonyl and trifluoromethyl);
$R_4$ is hydrogen, lower-alkyl, hydroxy, lower-alkoxy or halogen at the 4-, 5-, 6- or 7-positions;
m is 1 or 2
Alk is lower-alkylene containing from one to four carbon atoms which may contain a lower-alkyl group;
Het is an aliphatic heterocycle selected from the group consisting of 2- or 3-morpholinyl (or 2- or 3-morpholinyl substituted on any available carbon atom thereof by lower-alkyl and 2- or 3-thiomorpholinyl (or the S-oxides thereof, or 2- or 3-thiomorpholinyl, or the S-oxides thereof, substituted on any available ring carbon atom thereof by lower-alkyl), where each of said Het groups may be either unsubstituted on the nitrogen atom thereof or substituted thereon by a lower-alkyl, benzyl, lower-alkoxybenzyl or benzhydryl group; and
n is 0 or 1, except that n is not 0 when the Alk moiety is attached to a ring carbon atom adjacent to a ring N, O or S atom of a Het group; and (B) pharmaceutically-acceptable acid-addition and lower-alkyl quaternary ammonium salts thereof.

2. A compound according to claim 1 where:
$R_3$ is phenyl (or phenyl substituted by from one to two substituents selected from halogen, lower-alkoxy, hydroxy, lower-alkyl, nitro, amino, lower-alkylmercapto and lower-alkylsulfinyl) or 1-naphthyl; and
Het is 2- or 3-morpholinyl, 5-lower-alkyl-2- or 3-morpholinyl, 2- or 3-thiomorpholinyl (or the S-oxides thereof) or 5-lower-alkyl-2- or 3-thiomorpholinyl, where each of said Het groups may be either unsubstituted on the nitrogen atom thereof or substituted thereon by a lower-alkyl, benzyl, lower-alkoxybenzyl or benzhydryl group.

3. A compound according to claim 2 where n is 0.

4. A compound according to claim 2 where n is 1 and Alk is CHR', where R' is hydrogen or lower-alkyl.

5. A compound according to claim 2 where n is 1 and Alk is $CH_2CH_2$.

6. A compound according to claim 2 where:
$R_4$ is hydrogen or halogen at the 4-, 5-, 6- or 7-positions; and
Het is 2- or 3-morpholinyl or 2- or 3-thiomorpholinyl (or the S-oxides thereof), where each of said Het groups may be either unsubstituted on the nitrogen atom thereof or substituted thereon by a lower-alkyl, benzyl, 4-lower-alkoxybenzyl or benzhydryl group.

7. A compound according to claim 6 where:
$R_3$ is lower-alkoxy-phenyl or 1-naphthyl;
$R_4$ is hydrogen or 5-fluoro; and
Het is 4-lower-alkyl-2-morpholinyl or 4-lower-alkyl-2- or 3-thiomorpholinyl, or the S-oxides thereof.

8. A compound according to claim 7 where n is 0.

9. A compound according to claim 7 where n is 1 and Alk is CHR', where R' is hydrogen or lower-alkyl.

10. A compound according to claim 7 where n is 1 and Alk is 1,2-ethylene.

11. 2-Methyl-3-(4-methoxybenzoyl)-1-[(4-methyl-2-morpholinyl)methyl]-1H-indole according to claim 9.

12. 2-Methyl-3-(4-methoxybenzoyl)-1-[(4-methyl-3-thiomorpholinyl)methyl]-1H-indole according to claim 9.

13. 2-Methyl-3-(4-methoxybenzoyl)-1-[(4-methyl-2-thiomorpholinyl)methyl]-1H-indole according to claim 9.

14. 2-Methyl-3-(4-methoxybenzoyl)-1-[(4-methyl-3-thiomorpholinyl)methyl]-1H-indole S-oxide according to claim 9.

15. A method for the relief of pain, rheumatic or inflammatory conditions which comprises administering to a patient in need of such relief an effective analgesic, anti-rheumatic or anti-inflammatory amount of a 2-$R_2$-$R_4$-substituted-3-$R_3$-CO-1-[Het(Alk)$_n$]-1H-indole according to claim 1.

16. A method according to claim 15 wherein:
$R_3$ is lower-alkoxyphenyl or 1-naphthyl;
$R_4$ is hydrogen or 5-fluoro; and
Het is 4-lower-alkyl-2-morpholinyl or 4-lower-alkyl-2- or 3-thiomorpholinyl, or the S-oxides thereof.

17. A composition for the relief of pain, rheumatic or inflammatory conditions which comprises, as the active component thereof, an effective analgesic, antirheumatic or antiinflammatory amount of a 2-$R_2$-$R_4$-substituted-3-$R_3$-CO-1-[Het(Alk)$_n$]-1H-indole according to claim 1 together with a pharmaceutically acceptable excipient.

18. A composition according to claim 17 where:
$R_3$ is lower-alkoxy-phenyl or 1-naphthyl;
$R_4$ is hydrogen or 5-fluoro; and
Het is 4-lower-alkyl-2-morpholinyl or 4-lower-alkyl-2- or 3-thiomorpholinyl, or the S-oxides thereof.

* * * * *

UNITED STATES PATENT AND TRADEMARK OFFICE
CERTIFICATE OF CORRECTION

PATENT NO. : 5,068,234                          Page 1 of 2

DATED : November 26, 1991

INVENTOR(S) : Thomas E. D'Ambra, Edward R. Bacon, Malcolm R. Bell

It is certified that error appears in the above-identified patent and that said Letters Patent is hereby corrected as shown below: On title page, item [75]

Philip M. Carabateas, Michael A. Eissenstat, Virendra Kumar, John P. Mallamo and Susan J. Ward should NOT be listed as inventors.

Abstract: "herteryl" should read -- heteryl --.

Column 2, line 12: "1-](-methyl" should read -- 1-[(1-methyl --.

Column 4, line 11: "1-halo-3-R-2" should read -- 1-halo-3-$R_5$-2 --.

Column 4, line 16: "{k2-hydroxy" should read -- {2-hydroxy --.

Column 6, line 5: " -thiomor-" should read -- 3-thiomor- --.

Column 6, line 9: "4thiazepinyl" should read -- 4-thiazepinyl --.

Column 10, line 65: "(Alk)n" should read --- $(Alk)_n$ --.

Column 15, line 20: "X'" should read -- HO --.

Column 23, line 29: "added, hours" should read -- added, the mixture was heated under reflux for an additional two hours --.

Column 25, line 30: "1-(1-methyl" should read -- 1-[(1-methyl --.

Column 25, line 39: "6 g" should read -- 16 g --.

Column 28, line 34: "Preparation 3A" should read -- The Compounds of Formula V --.

UNITED STATES PATENT AND TRADEMARK OFFICE
CERTIFICATE OF CORRECTION

PATENT NO. : 5,068,234

DATED : November 26, 1991

INVENTOR(S) : Thomas E. D'Ambra, Edward R. Bacon, Malcolm R. Bell

It is certified that error appears in the above-identified patent and that said Letters Patent is hereby corrected as shown below:

Column 34, line 23: "solic" should read -- solid --.

Column 34, line 49: "MCD" should read -- MDC --.

Column 34, line 50: "760" should read -- 750 --.

Column 36, line 26: "(d)-1-(4-" should read -- (d)-1-[(4- --.

Column 46, line 9: 125° α 126°C should read -- 125°-126°C.

Column 50, line 21: "lower-alkyl and" should read -- lower-alkyl) and --.

Signed and Sealed this

Eighth Day of February, 1994

Attest:

BRUCE LEHMAN

Attesting Officer

Commissioner of Patents and Trademarks